US010545096B1

(12) United States Patent
Putman et al.

(10) Patent No.: US 10,545,096 B1
(45) Date of Patent: Jan. 28, 2020

(54) MARCO INSPECTION SYSTEMS, APPARATUS AND METHODS

(71) Applicant: Nanotronics Imaging, Inc., Cuyahoga Falls, OH (US)

(72) Inventors: Matthew C. Putman, Brooklyn, NY (US); John B. Putman, Celebration, FL (US); John Moffitt, Los Banos, CA (US); Michael Moskie, San Jose, CA (US); Jeffrey Andresen, Gilroy, CA (US); Scott Pozzi-Loyola, Watsonville, CA (US); Julie Orlando, Akron, OH (US)

(73) Assignee: NANOTRONICS IMAGING, INC., Cuyahoga Falls, OH (US)

( * ) Notice: Subject to any disclaimer, the term of this patent is extended or adjusted under 35 U.S.C. 154(b) by 0 days.

(21) Appl. No.: 16/262,017

(22) Filed: Jan. 30, 2019

Related U.S. Application Data

(60) Provisional application No. 62/744,478, filed on Oct. 11, 2018.

(51) Int. Cl.
*G01N 21/88* (2006.01)
*G01N 21/00* (2006.01)
(Continued)

(52) U.S. Cl.
CPC ......... *G01N 21/8806* (2013.01); *G02B 21/06* (2013.01); *G02B 21/26* (2013.01); *G02B 21/365* (2013.01); *G01N 2021/8835* (2013.01)

(58) Field of Classification Search
CPC ....... G01N 21/8806; G01N 2021/8835; G02B 21/06; G02B 21/365
See application file for complete search history.

(56) References Cited

U.S. PATENT DOCUMENTS 4,647,764 A * 3/1987 Chadwick ............ G02B 21/241
250/216
5,172,005 A 12/1992 Cochran et al.
(Continued)

FOREIGN PATENT DOCUMENTS

JP 12136916 5/2000
JP 15243465 8/2003
(Continued)

OTHER PUBLICATIONS

International Search Report on International Application No. PCT/US2007/024224; dated May 9, 2008.
(Continued)

*Primary Examiner* — Sang H Nguyen
(74) *Attorney, Agent, or Firm* — Polsinelli PC

(57) ABSTRACT

The disclosed technology relates to an inspection apparatus that includes a stage configured to retain a specimen for inspection, an imaging device having a field of view encompassing at least a portion of the stage to view a specimen retained on the stage, a lens having a view encompassing the specimen retained on the stage, and a plurality of lights disposed on a moveable platform. The inspection apparatus can further include a control module configured to control a position of the stage, an elevation of the moveable platform, and a focus of the lens. In some implementations, the inspection apparatus includes an image processing system configured for receiving image data from the imaging device, analyzing the image data to determine a specimen classification, and automatically selecting an illumination profile based on the specimen classification. Methods and machine-readable media are also contemplated.

6 Claims, 20 Drawing Sheets

(51) Int. Cl.
   *G02B 21/06*    (2006.01)
   *G02B 21/26*    (2006.01)
   *G02B 21/36*    (2006.01)

(56)     References Cited

U.S. PATENT DOCUMENTS

| | | | |
|---|---|---|---|
| 5,829,698 A | 11/1998 | Canada | |
| 5,917,588 A | 6/1999 | Addiego | |
| 6,021,380 A | 2/2000 | Fredriksen et al. | |
| 6,630,996 B2* | 10/2003 | Rao | G01N 21/9501 356/237.1 |
| 7,176,433 B1 | 2/2007 | Rosengaus | |
| 7,227,628 B1* | 6/2007 | Sullivan | G01N 21/9501 250/559.46 |
| 7,457,446 B2* | 11/2008 | Soenksen | G02B 21/002 382/128 |
| 7,724,362 B1 | 5/2010 | Rosengaus | |
| 10,048,477 B1 | 8/2018 | Putman et al. | |
| 2006/0199287 A1* | 9/2006 | Fu | G01N 21/9501 438/16 |
| 2010/0039818 A1* | 2/2010 | Haddock | A47G 1/12 362/253 |
| 2012/0013899 A1* | 1/2012 | Amanullah | G01N 21/9501 356/237.5 |
| 2014/0319379 A1* | 10/2014 | Manian | G01N 21/6428 250/459.1 |

FOREIGN PATENT DOCUMENTS

JP           1824969        10/2006
WO     20091020456 A1     2/2009

OTHER PUBLICATIONS

Barbara Zitova, "Image Registration Methods: A Survey," Image and Vision Computing, Oct. 11. 2003, vol. 21. Issue 11, pp. 977-1000.

NWL200—Nikon's Newest and Most Sophisticated Wafer Loader for IC Inspection Microscopes; NWL200 Upright Microscopes Industrial Microscopes; Nikon Metrology; Aug. 15, 2018.

MIL—micro & MACRO inspection loader; Microscope automatic loader with frontside and backside wafer inspection: SemiSyn; Aug. 15, 2018.

* cited by examiner

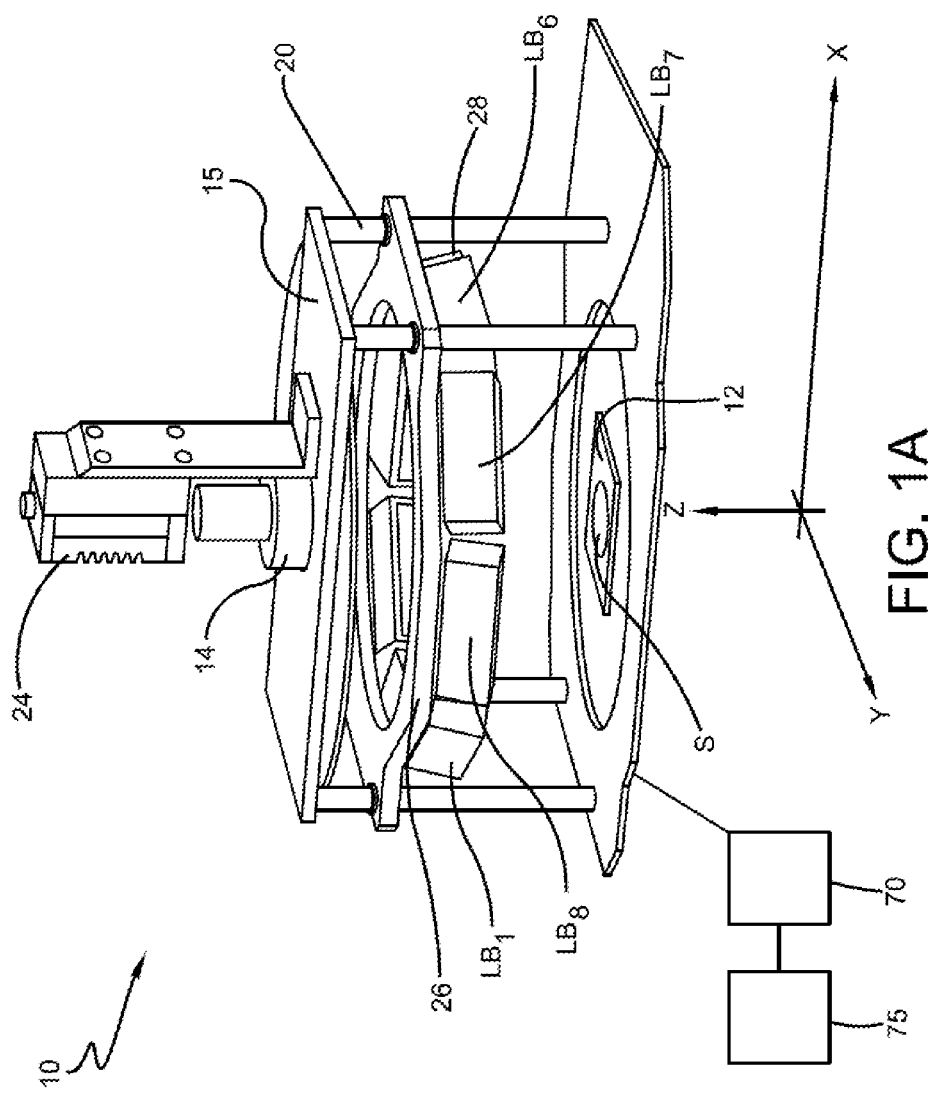

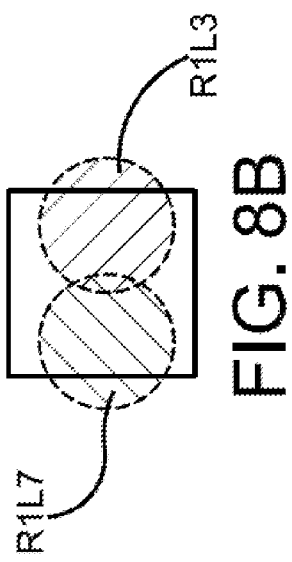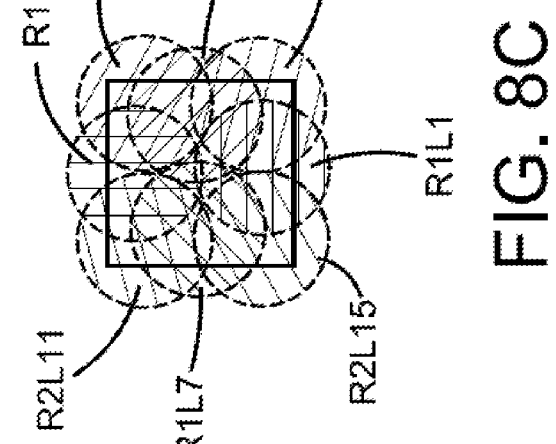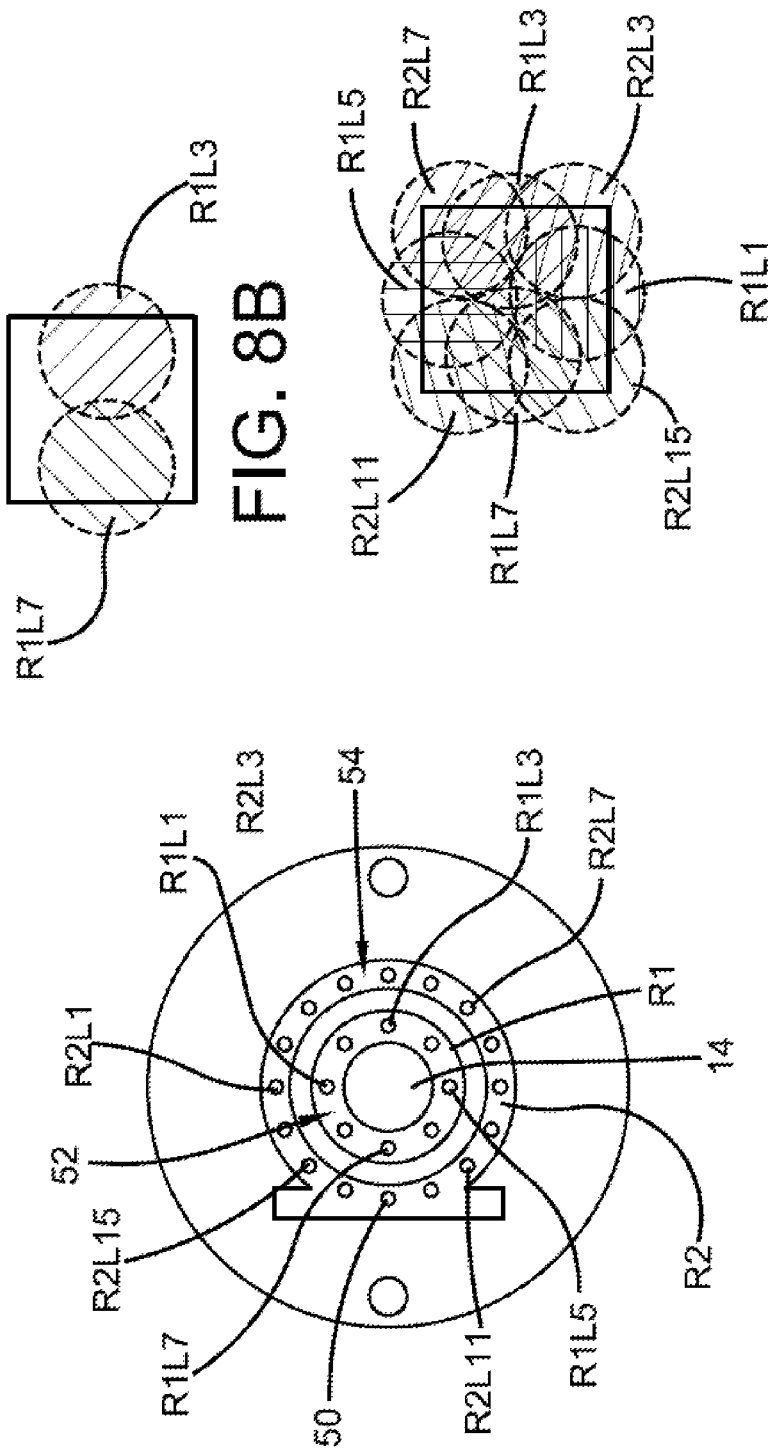

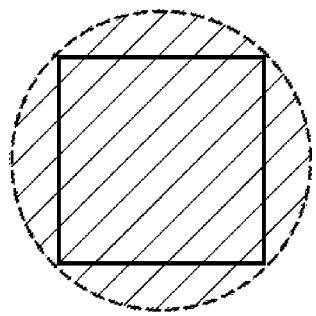
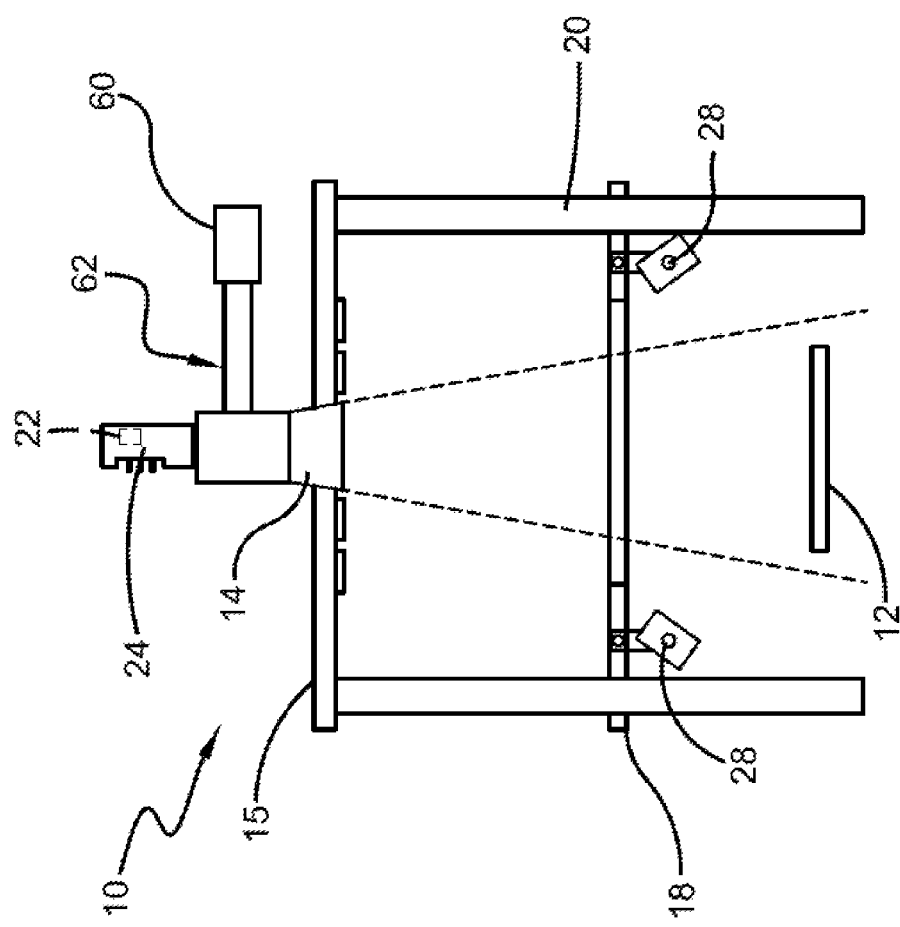
FIG. 9B
FIG. 9A

MARCO INSPECTION SYSTEMS, APPARATUS AND METHODS

This application claims the benefit of U.S. Provisional Application No. 62/744,478, filed Oct. 11, 2018, entitled "Macro Inspection Apparatus and Methods", which is incorporated by reference in its entirety.

TECHNICAL FIELD

The present disclosure generally relates to macro inspection systems, apparatus and methods. More particularly, embodiments of the present invention relate to macro inspection apparatus having multiple modes of illumination that can each provide variable illumination landscapes to detect features on a specimen.

BACKGROUND OF THE INVENTION

Microscopic examination of a specimen to detect specimen features can be limited. Specimens as understood by a person of ordinary skill in the art refer to an article of examination (e.g., a wafer or a biological slide), and features refer to known characteristics of a specimen, as well as abnormalities and/or defects. Features can include but are not limited to: circuits, circuit board components, biological cells, tissue, defects (e.g., scratches, dust, fingerprints). In some cases, features of a specimen are distributed across relatively large surface areas, or a specimen itself is rather large. For such specimens, microscopic examination can be insufficient or undesirable, because such examination acquires information over relatively small surface areas and requires the capture of multiple images of discrete portions of a specimen in order to represent the entire specimen. In addition, microscopic examination can be limited in the type and variety of illumination it can provide. For purposes of this specification, microscopic refers to an area less than 0.5 $cm^2$.

Accordingly, it is desirable to provide a new mechanism for macroscopic examination of a specimen that can capture the entire or large areas of a specimen in a single field of view and can provide for multiple modes of illumination including, but not limited to brightfield, darkfield or oblique illumination; polarized light; cross-polarized light; and differential interference contrast (DIC), phase contrast. It is also desirable that each mode of illumination provide variable illumination landscapes, as explained herein, to detect features of a specimen. For purposes of this specification, macroscopic refers to an area 0.5 $cm^2$ or greater.

SUMMARY OF INVENTION

In some aspects, the disclosed technology relates to an inspection apparatus that includes a stage configured to retain a specimen for inspection, an imaging device having a field of view encompassing at least a portion of the stage to view a specimen retained on the stage, and a lens having a field of view encompassing at least a portion of the specimen retained on the stage, and a plurality of lights disposed on a moveable platform. The inspection apparatus can further include a control module coupled to the imaging device, the stage, the moveable platform, and the lens, wherein the control module is configured to control a position of the stage, an elevation of the moveable platform, and a focus of the lens. In some implementations, the inspection apparatus can further include an image processing system coupled to the control module, wherein the image processing system includes one or more processors and a non-transitory media comprising instructions that are configured to cause the processors to perform operations for: receiving image data from the imaging device, wherein the image data corresponds with at least a partial view of the specimen retained on the stage, analyzing the image data to determine a specimen classification corresponding with the specimen retained on the stage, automatically selecting an illumination profile based on the specimen classification.

In another aspect, the disclosed technology relates to an inspection apparatus including a stage configured to retain a specimen for inspection, an imaging device having a field of view encompassing at least a portion of the stage to view light reflected by a specimen retained on the stage, and a plurality of lights disposed on a moveable platform. Depending on the desired implementation, the inspection apparatus can further include a control module coupled to the imaging device, each of the lights and the moveable platform, wherein the control module is configured to perform operations including: receiving image data from the imaging device, wherein the image data indicates an illumination landscape of light incident on the specimen, automatically adjusting an elevation of the moveable platform or an intensity of one or more of the plurality of lights to improve the illumination landscape, based on the image data.

In yet another aspect, the disclosed technology can encompass a computer implemented-method for automatically adjusting an illumination landscape provided by an inspection apparatus. The method can include steps for receiving image data from an imaging device, wherein the image data corresponds with at least a partial view of a specimen retained on a stage of the inspection apparatus, analyzing the image data to determine a specimen classification corresponding with the specimen retained on the stage, automatically selecting an illumination profile based on the specimen classification.

BRIEF DESCRIPTION OF THE DRAWINGS

In order to describe the manner in which the above-recited and other advantages and features of the disclosure can be obtained, a more particular description of the principles briefly described above will be rendered by reference to specific embodiments thereof which are illustrated in the appended drawings. Understanding that these drawings depict only exemplary embodiments of the disclosure and are not therefore to be considered to be limiting in their scope, the principles herein are described and explained with additional specificity and detail through the use of the accompanying drawings in which:

FIG. 1A shows a perspective view of a particular embodiment of a macro inspection apparatus;

FIG. 8A shows an example implementation of first and second arrays of brightfield lights;

FIG. 8B shows an example of substantially orthogonal illumination employing 2 lights;

FIG. 8C shows an example of substantially orthogonal illumination employing 7 lights;

FIG. 9A shows a schematic side view of a macro inspection apparatus employing orthogonal illumination through the lens;

FIG. 9B shows an example of orthogonal illumination as established by the operation of the apparatus per FIG. 9A;

DETAILED DESCRIPTION OF ILLUSTRATIVE EMBODIMENTS

In accordance with some embodiments of the disclosed subject matter, mechanisms (which can include systems, methods, devices, apparatuses, etc.) for macroscopic inspection of specimens are provided. Macroscopic examination (sometimes referred to as inspection) refers to scanning, imaging, analyzing, measuring and any other suitable review of a specimen using the disclosed macroscopic inspection mechanism. The disclosed macroscopic inspection mechanism includes one or more modes of illumination that can each provide variable illumination landscapes, as described herein. Although the following description refers to components and methods implemented in a macroscopic inspection mechanism, the components and methods described herein can also be implemented in a microscope inspection system.

Figure 1B:
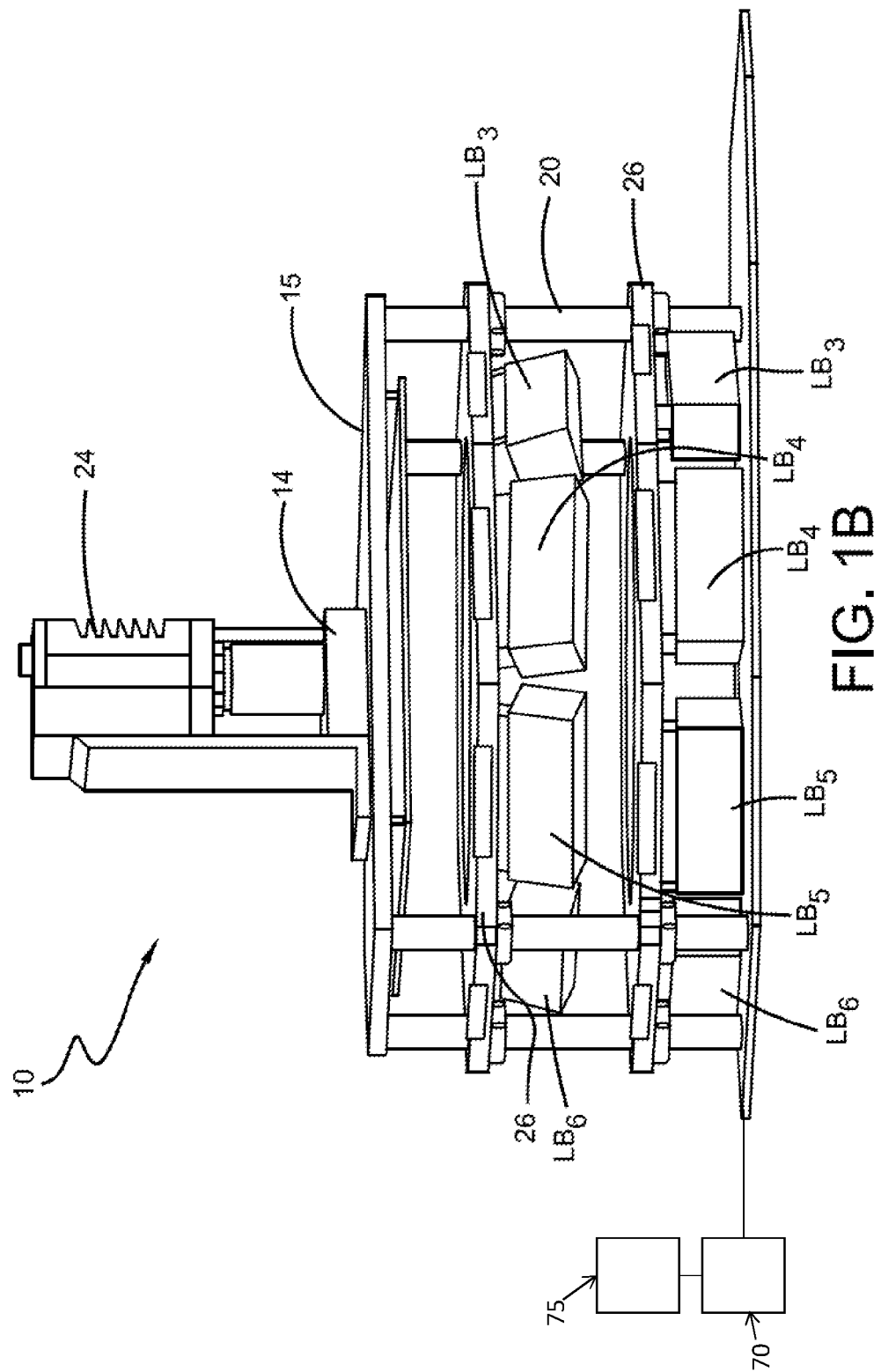
FIG. 1B shows a perspective view of a particular embodiment of a macro inspection apparatus.
Figure 1C:
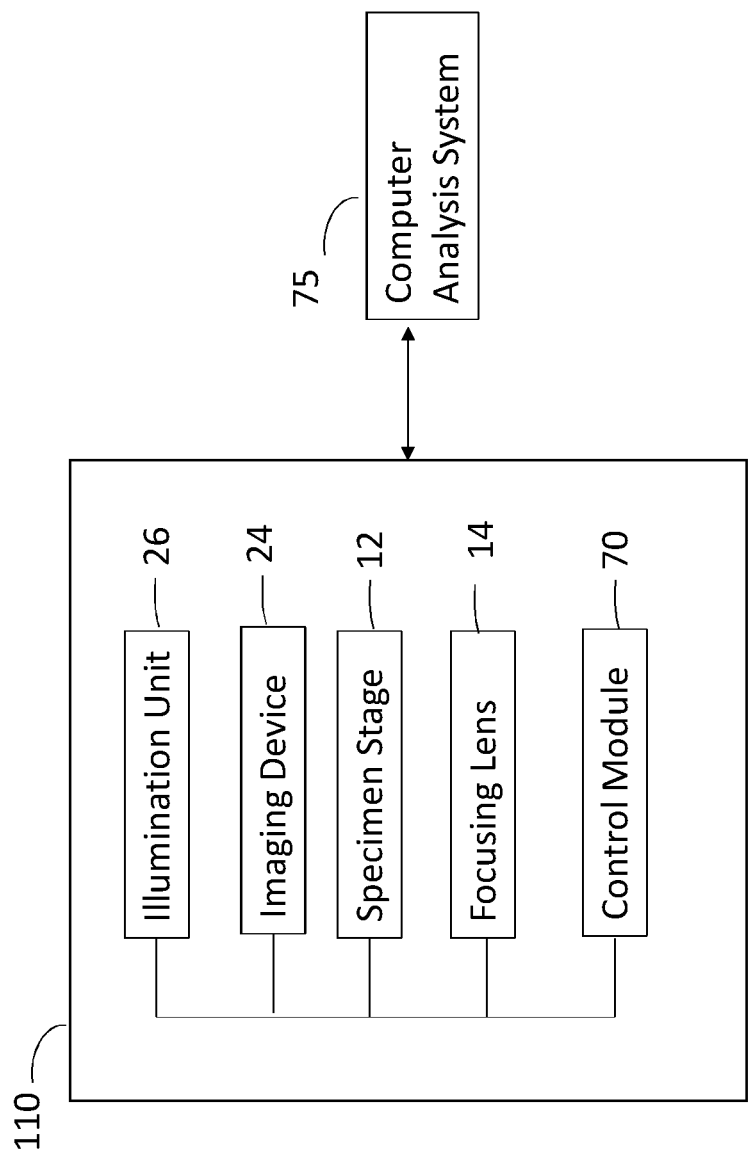
FIG. 1C shows a particular embodiment of a macro inspection apparatus.

FIGS. 1A, 1B and 1C illustrate examples of a macro inspection system 10 according to some embodiments of the disclosed subject matter. At a high level, the basic components of macro inspection system 10, according to some embodiments, include an illumination unit (e.g., light assembly ring 26) for providing light to a specimen S, a focusing lens 14, an imaging device 24, a specimen stage 12, a control module 70 comprising hardware, software, and/or firmware and a computer analysis system 75. Macro inspection system 10 can be implemented as part of an optical inspection system that uses transmitted or reflected light.

Figures 5A, 5B, 5C:
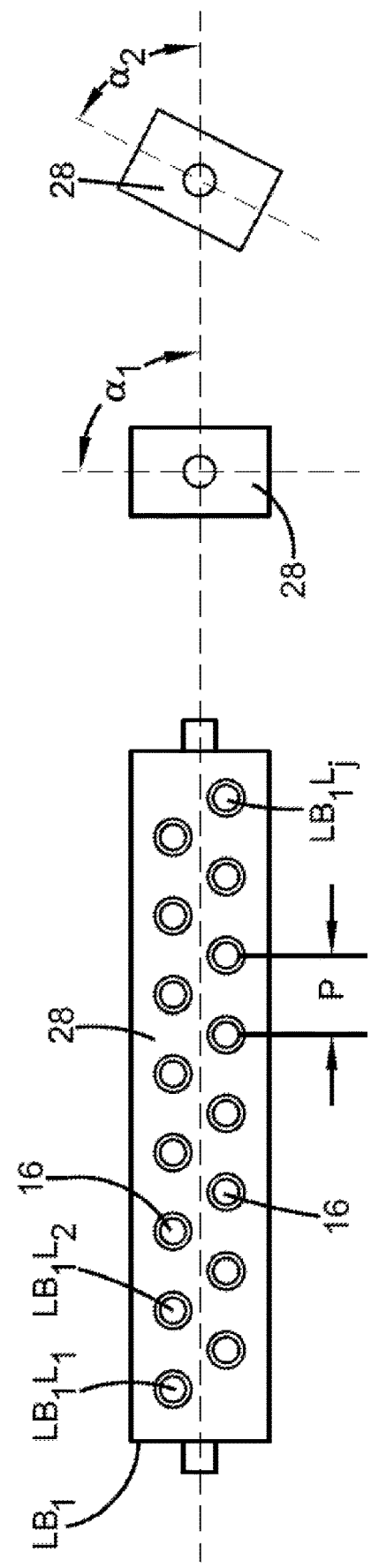
FIG. 5A shows a front view of an exemplary light bar.
FIGS. 5B and 5C show side views of the light bar of FIG. 6A, showing an ability to pivot as at angles α1 and α2.

In some embodiments, as shown in FIG. 1A, a light assembly ring 26 can be used as an illumination unit for macro inspection system 10. One or more light fixtures, e.g., light bars 28, represented by $LB_1$ to $LB_x$, can be mounted to light assembly ring 26. Note, any type of suitable light fixture can be mounted to light assembly ring 26. As shown in FIG. 1A, light assembly ring 26 can be configured so that the individual one or more light bars 28 mounted to the assembly are positioned radially outside of the perimeter of specimen stage 12. Each light bar 28 can include one or more plurality of lights 16 (as shown in FIG. 5A). Macro inspection system 10 can also include more than one light assembly ring 26, as shown for example in FIG. 1B.

In some embodiments, light assembly ring 26 can be configured so that it is movable along guiderails 20. Note, that the illumination unit is not limited to a ring formation, and individual light bars 28 can be mounted in other types of formations to a non-moveable or moveable platform 18 as shown, for example in FIGS. 2A, 3A, 7A and 9A. Further, the movement of movable platform 18 to different positions along the height of the guiderails 20 can be controlled manually, or automatically by software, hardware, and/or firmware (e.g., control module 70). Depending on its height in relation to specimen stage 12, light assembly ring 26 can be used to provide oblique or darkfield illumination to a specimen when retained on specimen stage 12. For example, to provide variable angles of oblique illumination, light assembly ring 26 can be positioned so that its light can be projected at different heights above a specimen plane (i.e., the top planar surface of a specimen when positioned on specimen stage 12). In some embodiments, the specimen plane corresponds with a focal plane of macro inspection system 10 (i.e., the plane where the specimen is in focus). In further examples, to provide darkfield illumination, light assembly ring 26 can be positioned so that its light can be projected at the same, or substantially the same, level of the specimen plane of a specimen on specimen stage 12 to provide darkfield illumination to a specimen when retained on specimen stage 12.

As used herein: oblique illumination refers to light projected toward the specimen at an angle of incidence less than 90 degrees and greater than 0 degrees, typically greater than 1 degrees; darkfield illumination refers to light projected toward the specimen at an angle of incidence less than 1 degrees and typically 0 degrees; and brightfield illumination refers to light projected toward the specimen at an angle of incidence perpendicular (90 degrees) to the plane of the specimen. Brightfield illumination can refer to a light source that provides illumination through lens 14 towards a specimen in an orthogonal direction ("orthogonal illumination"), as shown for example in FIG. 9A, or to a light source positioned outside lens 14 that projects light in a "substantially orthogonal" direction ("substantially orthogonal illumination"), as shown, for example, in FIGS. 7A and 8A.

Figure 2B:
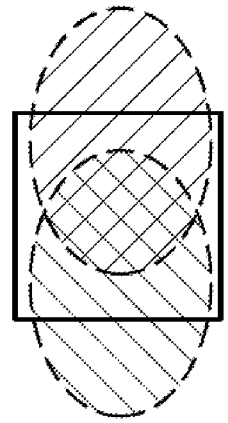
FIG. 2B shows an example of the low angle oblique illumination as established by the operation of the apparatus per FIG. 2A.
Figure 2A:
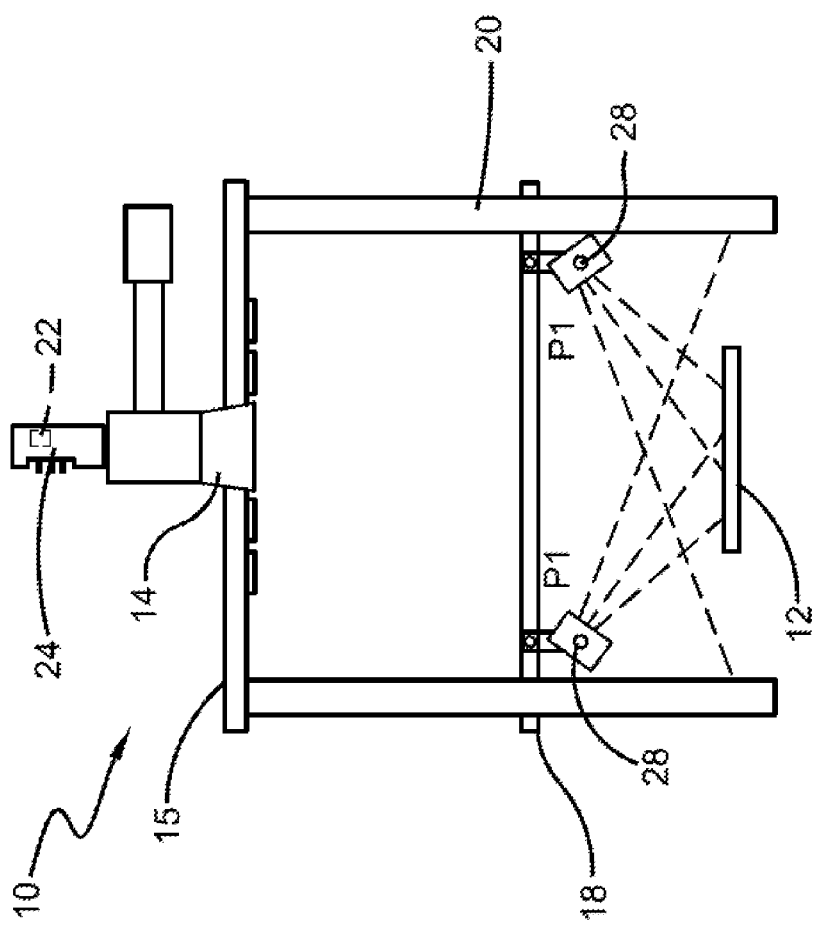
FIG. 2A shows a schematic side view of an embodiment of a macro inspection apparatus providing oblique illumination from a low angle of incidence.
Figure 3B:
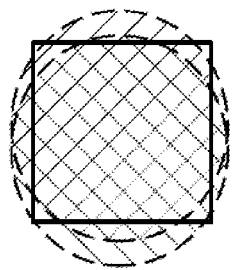
FIG. 3B shows an example of high angle oblique illumination as established by the operation of the apparatus per FIG. 3A.
Figure 3A:
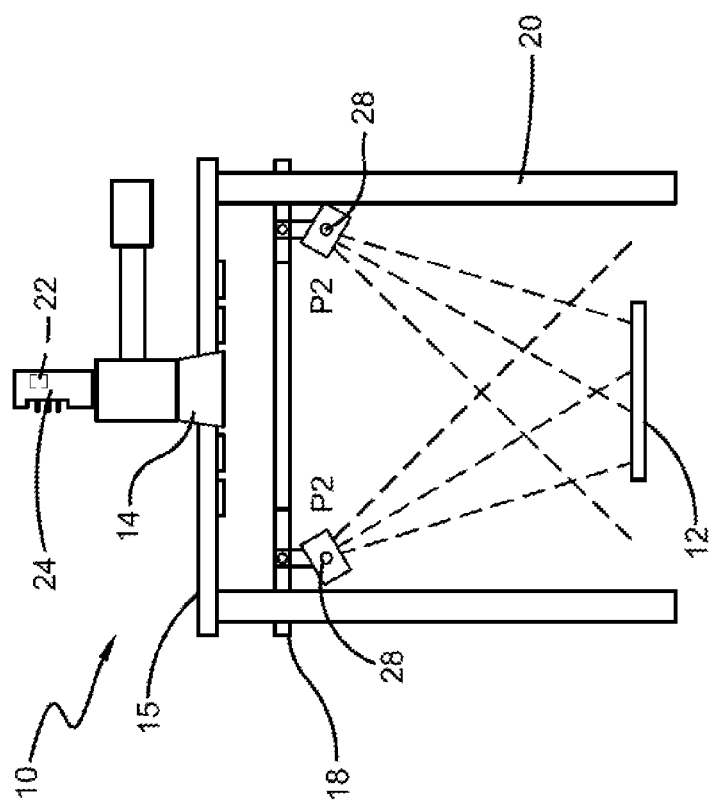
FIG. 3A shows a schematic side view of an embodiment of a macro inspection apparatus providing oblique illumination from a high angle of incidence.

As shown in FIGS. 2A and 3A, each light bar 28 can provide oblique lighting at different angles of incidence, from multiple directions, in accordance with some embodiments of the disclosed subject matter. For example, as illustrated in FIG. 2A, each light bar 28 is supported over the specimen plane of specimen stage 12 at a first position P1 providing for oblique illumination at a first angle of incidence, while, in FIG. 3A, each light bar 28 has been moved upward to position P2 to provide oblique illumination at a second angle of incidence. Moving the light fixture upward can cause the angle of incidence to increase. The resultant illumination of stage 12 is shown in FIGS. 2B and 3B. In some embodiments, at each height of moveable platform 18 along guiderails 20, light bar 28 can be selectively pivotable about a pivot point as shown for example in FIGS. 5B and 5C to create varied angles of illumination relative to the specimen plane of a specimen when retained on specimen stage 12. Note, a person of ordinary skill in the art will readily understand that the oblique lighting shown in FIGS. 2A and 3A, can be implemented with a single or multiple light bars 28.

Figure 4B:
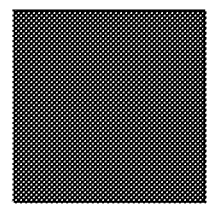
FIG. 4B shows an example of darkfield illumination as established by the operation of the apparatus per FIG. 4A.
Figure 4A:
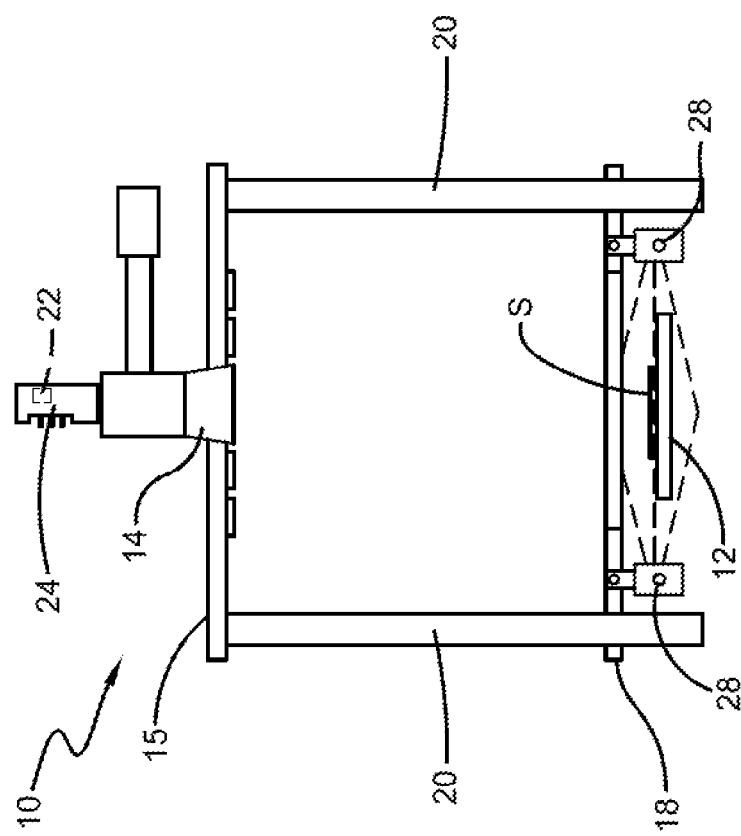
FIG. 4A shows a schematic view of a macro inspection apparatus operating in a darkfield illumination mode.

In some embodiments, as shown in FIG. 4A, light bars 28 can be positioned so that illumination from light bar 28 is substantially parallel to a specimen plane to provide darkfield illumination to a specimen when retained on specimen stage 12. Substantially parallel is to be understood as having an angle of incidence from −1° to +1°, to allow for imperfections in alignment, but in some embodiments, the illumination will be on plane, i.e., at an angle of incidence of 0°, whereby illumination will be reflected only if there are features extending off of a perfectly flat planar surface of a specimen. If a specimen is perfectly flat and featureless, then it would not reflect any of the substantially parallel illumination to lens 14, and such a specimen viewed by lens 14 (as shown in FIG. 4B) will not be illuminated. If there are protruding imperfections or other features, then the illumination from light bar 28 will reflect off of such imperfections and/or features and will be captured by image sensor 22 via lens 14. Note, a person of ordinary skill in the art will readily understand that the darkfield illumination shown in FIG. 4A, can be implemented with a single or multiple light bars 28.

In some embodiments, an XY translation stage can be used for specimen stage 12. Specimen stage 12 can be driven by stepper motor, server motor, linear motor, piezo motor, and/or any other suitable mechanism, including a manual mechanism. Specimen stage 12 can be configured to move an object in the X axis and/or Y axis directions under the control of any suitable controller (e.g., control module 70), in some embodiments. An actuator (not shown but known in the art) can be used to make coarse focus adjustments of, for example, 0 to 5 mm, 0 to 10 mm, 0 to 30 mm, and/or any other suitable range(s) of distances. An actuator can also be used in some embodiments to provide fine focus of, for example, 0 to 50 µm, 0 to 100 µm, 0 to 200 µm, and/or any other suitable range(s) of distances.

In some embodiments, lens 14 can be supported on a lens stage 15 and can be positioned at an aperture through the lens stage above specimen stage 12. Further, macro inspection system 10 can include a focus mechanism that adjusts specimen stage 12 in a Z direction towards and away from lens 14 and/or adjusts lens 14 (e.g., via lens stage 15 along guiderails 20) towards and away from specimen stage 12. Movement of specimen stage 12 and/or lens 14 can be driven by stepper motor, server motor, linear motor, piezo motor, and/or any other suitable mechanism, including a manual mechanism. Lens 14 can have different magnification powers, and/or be configured to operate with brightfield, darkfield or oblique illumination, polarized light, cross-polarized light, differential interference contrast (DIC), phase contrast and/or any other suitable form of illumination. The type of lens used for macro inspection system 10 can be based on desired characteristics, for example, magnification, field of view, numerical aperture, among others. In some embodiments, lens 14 can be a macro lens that can be used to view a specimen within a single field of view. Note, the term field of view as understood by a person of ordinary skill in the art refers to an area of examination that is captured at once by an image sensor. Further, a person of ordinary skill in the art will readily understand that the terms field of view and image are used interchangeably herein.

The illumination of a specimen on specimen stage 12 reflects up to lens 14 mounted to an imaging device 24 (e.g., camera), and imaging device 24 can capture images and/or video of a specimen. In some embodiments, camera 24 can be a rotatable camera that includes an image sensor, configured to allow the camera to be aligned to a specimen, a stage and/or a feature on a specimen. The image sensor can be, for example, a charged-coupled device (CCD), a complementary metal-oxide semiconductor (CMOS) image sensor, and/or any other suitable electronic device that converts light into one or more electrical signals. Such electrical signals can be used to form images and/or video of an object. In some embodiments, such electrical signals are transmitted for display on a display screen connected to macro inspection system 10. Some example methods for rotating a camera that can be used by macro inspection system 10 are described in U.S. Pat. No. 10,048,477 entitled "Camera and Object Alignment to Facilitate Large Area Imaging in Microscopy," which is hereby incorporated by reference herein in its entirety. In some embodiments, imaging device 24 can be replaced with an ocular or an eyepiece that is used to view a specimen.

In some embodiments, as shown in FIG. 5A, a light bar comprises individual lights 16 organized in two rows. Individual lights 16 can be based on any type of suitable lighting technology, including but not limited to: light emitting diode (LED), organic light emitting diode (OLED), fluorescent, fiber optic, gas-plasma, cathode ray tube (CRT), liquid crystal display (LCD), laser, etc. In some embodiments, as shown in FIG. 5A, each light can be individually addressed by its light bar number and light number, as represented by $LB_iL_j$. In further embodiments, the lights can be divided into sections (e.g., by row, column, quadrant, light bar, and/or any other suitable division) and each section can be addressable. Software, hardware and/or firmware (e.g., control module 70) can control the activation, intensity and/or color of each light or section by its address. Activation refers to the turning on of a light, intensity refers to the rate at which light energy is delivered to a unit of surface, and color refers to an RGB (red, green, blue) color value, where each color value is specified as an integer from 0 to 255. Intensity can be determined by light meters, image sensors and/or other suitable intensity measurement devices. Plurality of lights 16 can be comprised of lights that project monochromatic, different colors, and/or any combination thereof.

Figure 6:
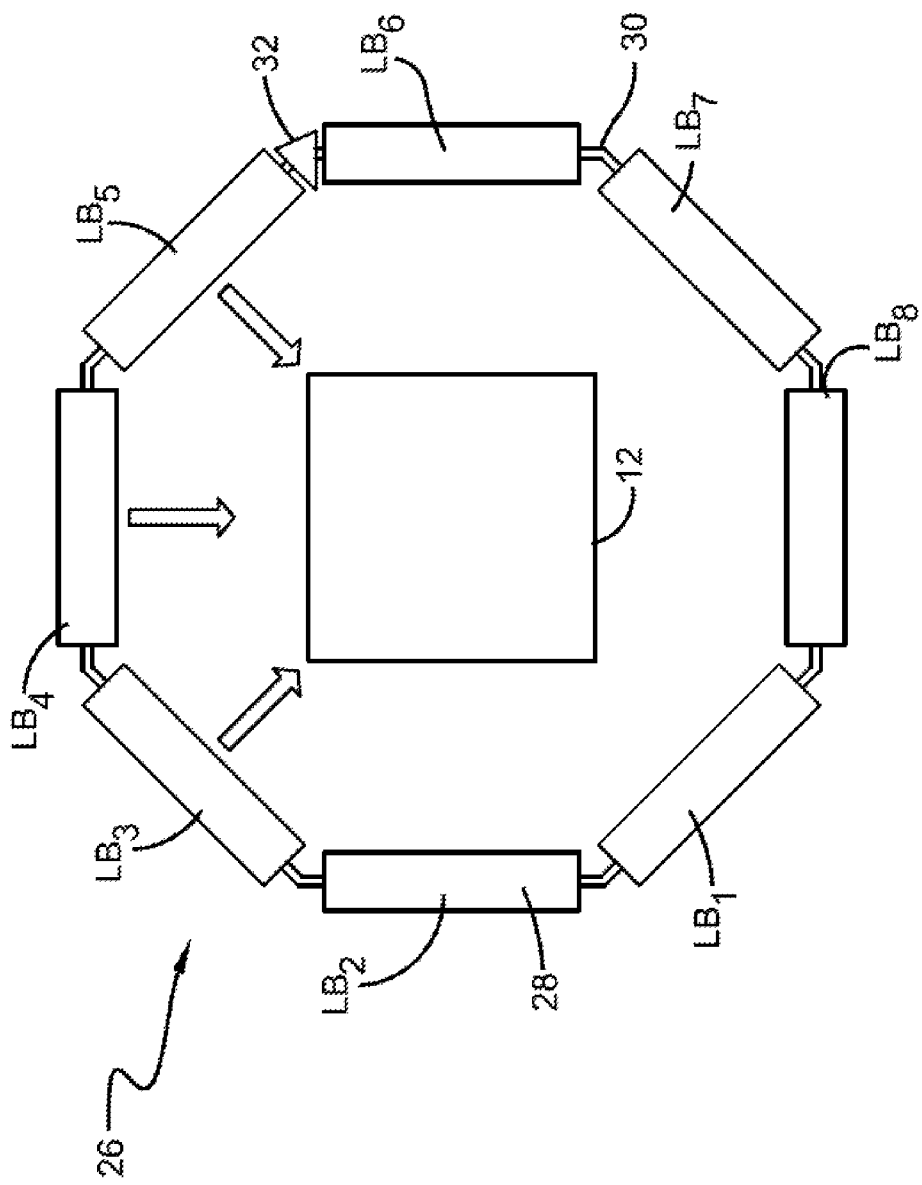
FIG. 6 shows a schematic top plan view of an embodiment of a light ring assembly employing multiple light bars for establishing various potential illumination vectors.

As shown in FIG. 6, in accordance with some embodiments of the disclosed subject matter, a plurality of light bars 28 (e.g., $LB_1$ to $LB_8$) can be positioned radially outside the perimeter of specimen stage 12 (e.g., in an octagonal shape creating a 360 degree circumference of lights) and can be selectively activated and illuminable by color and/or intensity to illuminate the specimen from different directions. Software, hardware and/or firmware (e.g., control module 70) can control which light bars and individual lights are activated and at what color and/or intensity. A single light 16, or multiple lights 16 from a single or multiple light bars 28 can be activated to illuminate a portion or an entire field of view at the specimen plane. The type of specimen being examined, the type of feature being examined, a region of interest on a specimen, and/or any other suitable criteria, can determine which lights are activated and at what color and/or intensity.

As shown in FIG. 6, according to some embodiments, one or more of light bars 28 can be connected to a neighboring light bar 28 with a universal joint 30 providing connectivity between neighboring light bars 28 so that they can be pivoted concurrently and at the same angle when one of the co-joined light bars is moved. In further embodiments, universal joints 30 can be used at every neighboring junction to allow for common movement of all light bars 28 and control by a single control mechanism (e.g., control mechanism 32). Software, hardware and/or firmware (e.g., control module 70) can control the pivoting of each light bar 28 individually or concurrently with one or more other light bars. In some embodiments, light bars 28 can be pivoted manually. Each light bar 28 can be pivoted the same or different amounts about a pivot point.

Each individual light 16 of a single light bar 28 (represented by $LB_iL_j$) can individually or together emit a vector of light to illuminate a particular area on the specimen plane ("area of illumination"). The magnitude of this area of illumination can vary from illuminating a portion of the specimen to encompassing the entire specimen plane. The area of illumination can be calculated at different axial locations above, below or on the specimen plane (e.g., at the top of specimen stage 12, at the top of the specimen plane, at the focal plane, etc.) along the beam of light represented by the vectors. The areas covered by each vector of light can either be overlapping in part with the areas covered by the vector of light emitted from a neighboring light bar or not overlapping at all. In some embodiments, one or more focusing lenses and/or collimating lenses can be used to focus the area of each light vector to a region suitable for a specimen on specimen stage 12.

In some embodiments, as shown for example in FIG. 6, multiple light bars are radially positioned around the perimeter of specimen stage 12 and are selectively illuminable to illuminate a specimen from different directions. Each light bar, according to some embodiments, can emit a single vector of light. FIG. 6 shows three illumination vectors of light emitted from light bars $LB_3$, $LB_4$ and $LB_5$ respectively. The size of the vector can vary, but each vector illuminates from a discrete direction of limited degrees (or minutes of arc) that is less than the entire 360 degree circumference of the radially positioned light bars that can project light towards a specimen on specimen stage 12. Each vector can illuminate at least a portion of the entire field of view, and in some embodiments, each vector can illuminate an entire field of view.

In some embodiments, a single illumination vector ranges from 1 degree or more to 180 degrees or less (60 or more to 10,800 or less minutes of arc). In other embodiments, a single illumination vector ranges from 45 degrees or more to 120 degrees or less (2,700 or more to 7,200 or less minutes of arc), in other embodiments, from 30 degrees or more to 45 degrees or less (1,800 or more to 2,700 or less minutes of arc), in other embodiments, from 10 degrees or more to 30 degrees or less (600 or more to 1,800 or less minutes of arc), in other embodiments, from 5 degrees or more to 10 degrees or less (300 or more to 600 or less minutes of arc), and, in other embodiments, from 2 degrees or more to 5 degrees or less (120 or more to 300 or less minutes of arc). The vector depends upon the number and position of activated lights of the at least one light bar 28 relative to the position of the specimen.

Light bar 28 can vary as to the number of lights 16, as represented by the number of rows and columns, the size of each individual light, the cone angle of each individual light, the pitch (p) between lights and the distance between the lights and the area where the light is projected. In some embodiments, the size of specimen stage 12, the specifications of lens 14, the size and/or type of specimen being inspected, and/or the features of a specimen that are being examined, can determine the configuration of lights on light bar 28, including, for example, the arrangement of lights (whether in rows and columns or in other arrangements), the total number of lights, the distance, and/or the pitch (p).

Figure 7B:
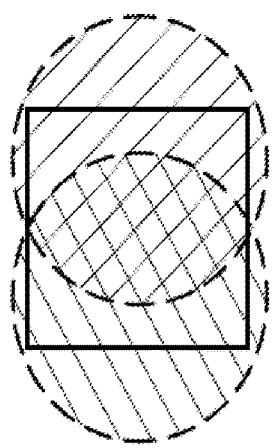
FIG. 7B shows an example of substantially orthogonal illumination as established by the operation of the apparatus per FIG. 7A.
Figure 7A:
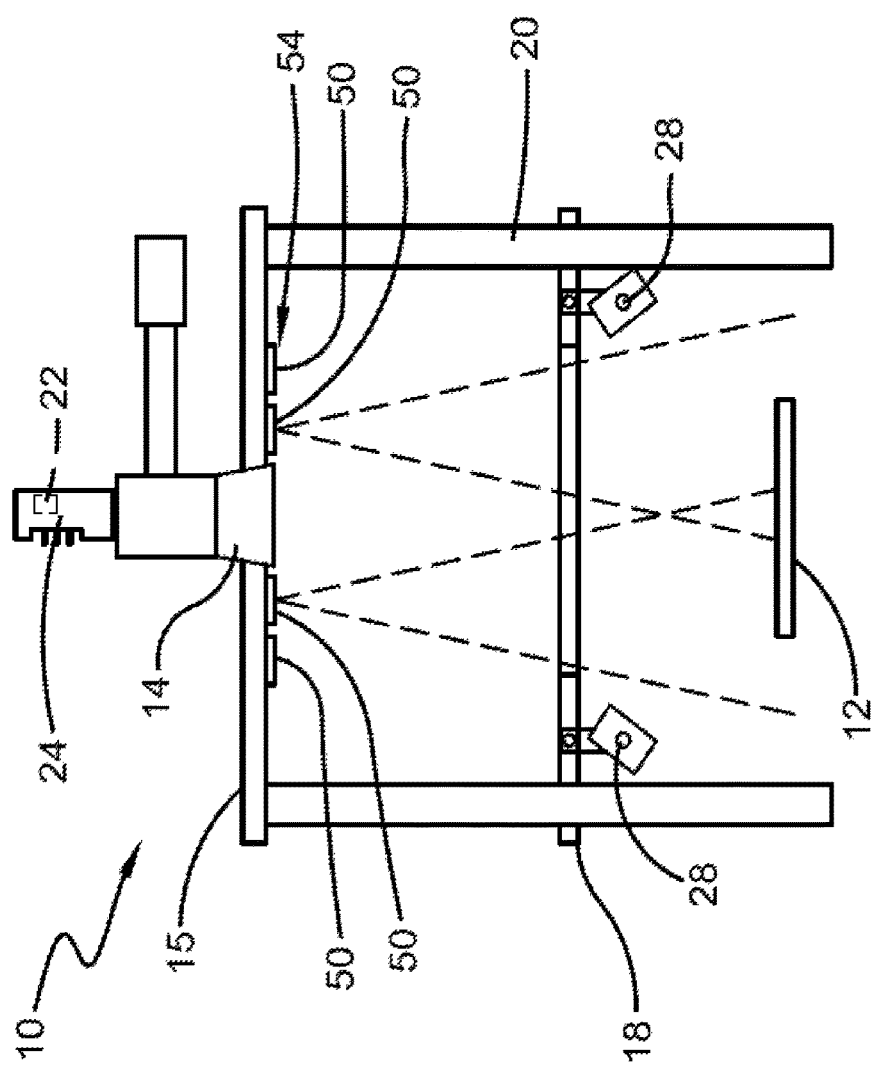
FIG. 7A shows a schematic side view of a macro inspection apparatus employing two opposed brightfield lights positioned to illuminate a specimen in a substantially orthogonal direction.

In some embodiments, as shown in FIG. 7A, macro inspection system 10 can also include one or more brightfield lights 50 positioned radially outside of lens 14 and directed to illuminate at least a portion of specimen S in a substantially orthogonal direction. By "substantially orthogonal" it is meant that the source of light is positioned outside of lens 14 and the projected light beam is perpendicular to the specimen and illuminates a portion or all of the specimen (e.g., as shown in FIG. 7B). Brightfield lights 50 can be deployed in various configurations outside of the lens 14 (e.g., radially or in a grid pattern). In particular embodiments, such as that shown in FIG. 8A, a plurality of brightfield lights 50 are arranged in a first array of brightfield lights 52, wherein each brightfield light of the first array is radially equidistant from the center of lens 14. While FIG. 8A provides an embodiment with a second array of brightfield lights 54, wherein each brightfield light 50 of second array 54 is radially equidistant from the center of lens 14, in some embodiments, a single array or more than two arrays can also be deployed. The second array in FIG. 8A is at a farther distance than the first. The arrays are shown as circular about the circumference of the lens 14, such that lights of the different arrays can be selected for illuminating the specimen from varying radial distances. Each light can be addressed, for example, by its array number and light number (e.g, $R_xL_y$). FIG. 8B shows the resultant illumination of specimen stage 12 when lights $R_1L_7$ and $R_1L_3$ are activated. FIG. 8C shows the resultant illumination of specimen stage 12 when lights $R_1L_7$, $R_2L_{11}$, $R_1L_5$, $R_2L_7$, $R_1L_3$, $R_1L_3$, $R_2L_3$, $R_1L_1$, $R_2L_{15}$, $R_1L_7$, $R_2L_{11}$ are activated.

As shown in FIG. 9A, in some embodiments, macro inspection system 10 includes light source 60 (which can include a single or plurality of lights) for providing selective illumination through lens 14 from a vertical illuminator 62 and orthogonally illuminating at least a portion of a specimen S. This illumination is termed "orthogonal" as it is directly above the specimen, whereas the brightfield illumination shown in FIGS. 7A and 8A emanate from light sources radially outside of lens 14 positioned over specimen S ("substantially orthogonal"). In some embodiments, as shown in FIG. 9B, the orthogonal light can encompass the entire specimen. A person of ordinary skill in the art will readily understand that orthogonal or substantially orthogonal light provided in FIGS. 7A, 8A and 9A can include polarized light, cross-polarization or differential interference contrast among other lighting techniques.

Similar to lights 16, each light 50 and/or 60 can be individually addressed. In further embodiments, the lights can be divided into sections (e.g., by array, quadrant, and/or any other suitable division) and each section can be addressable. Software, hardware and/or firmware (e.g., control module 70) can control the activation, intensity and/or color of each light or section by its address. Plurality of lights 50 and/or 60 can be comprised of lights that project monochromatic, different colors, and/or any combination thereof.

As should be generally appreciated from the examples of illumination in FIGS. 2B, 3B, 4B, 7B, 8B, 8C and 9B, the various embodiments of the present invention allow for darkfield illumination, illumination at variable oblique angles and brightfield illumination (both orthogonal and substantially orthogonal illumination).

In some embodiments, control module 70 includes a controller and controller interface, and can control any settings of macro inspection system 10 (e.g., intensity of lights 16, 50 and/or 60, color of lights 16, 50 and/or 60, turning on and off one or more lights 16, 50 and/or 60, pivoting or other movement of one or more light bars 28, movement of one or more light ring assemblies 26 (e.g., in a z direction), movement of specimen stage 12 (in x, y, and/or z directions), movement of lens 14, recording of image data by image sensor 22/camera 24, rotation or movement of camera 24, processing of illumination data, processing of image data). Control module 70 and applicable computing systems and components described herein can include any suitable hardware (which can execute software in some embodiments), such as, for example, computers, microprocessors, microcontrollers, application specific integrated circuits (ASICs), field-programmable gate arrays (FPGAs) and digital signal processors (DSPs) (any of which can be referred to as a hardware processor), encoders, circuitry to read encoders, memory devices (including one or more EPROMS, one or more EEPROMs, dynamic random access memory ("DRAM"), static random access memory ("SRAM"), and/or flash memory), and/or any other suitable hardware elements. In some embodiments, individual components within macro inspection system 10 can include their own software, firmware, and/or hardware to control the individual components and communicate with other components in macro inspection system 10.

In some embodiments, communication between the control module (e.g., the controller and controller interface) and the components of macro inspection system 10 can use any suitable communication technologies, such as analog technologies (e.g., relay logic), digital technologies (e.g., RS232, ethernet, or wireless), network technologies (e.g., local area network (LAN), a wide area network (WAN), the Internet, Bluetooth technologies, Near-field communication technologies, Secure RF technologies, and/or any other suitable communication technologies.

In some embodiments, operator inputs can be communicated to control module 440 using any suitable input device (e.g., keyboard, mouse, joystick, touch).

In some embodiments, control module 70 controls the activation, intensity and/or color of one or more of the plurality of lights 16, 50 and/or 60, as well as the position of lights 16 and/or light bar 28 (e.g., by adjusting a light bar's height, or by pivoting a light bar), light 50 and/or 60 (e.g., by adjusting the distance between lights 50 and/or 60 and the specimen plane) to provide for variable illumination landscapes on a specimen when it is placed on specimen stage 12. Illumination landscape refers to the color and/or intensity of light on a region of interest of a specimen as a result of the activation and distribution of light from the one or more of the plurality of lights 16, 50 and/or 60 that is directed towards a specimen. The illumination landscape can affect the image viewed through lens 14 and/or images captured by image sensor 22. Control module 70 can control the intensity of one or more of the plurality of lights 16, 50 and/or 60 to provide a desired illumination landscape on a specimen plane and/or specimen stage 12. For example, control module 70 can control the intensity of one or more of the plurality of lights 16, 50 and/or 60 to provide an illumination landscape of uniform intensity on a specimen plane and/or specimen stage 12. The type of illumination landscape provided can be determined by the specimen type, mechanical and/or physical properties of a specimen (e.g., specimen size, specimen reflectivity), a specimen feature being examined, a particular stage of a manufacturing and/or examining process, or some other suitable variable, individually or in any combination thereof.

In some embodiments, computer analysis system 75 can be coupled to, or included in, macro inspection system 10 in any suitable manner using any suitable communication technology, such as analog technologies (e.g., relay logic), digital technologies (e.g., RS232, ethernet, or wireless), network technologies (e.g., local area network (LAN), a wide area network (WAN), the Internet) Bluetooth technologies, Near-field communication technologies, Secure RF technologies, and/or any other suitable communication technologies. Computer analysis system 75, and the modules within computer analysis system 75, can be configured to perform a number of functions described further herein using images output by macro inspection system 10 and/or stored by computer readable media.

Computer analysis system 75 can include any suitable hardware (which can execute software in some embodiments), such as, for example, computers, microprocessors, microcontrollers, application specific integrated circuits (ASICs), field-programmable gate arrays (FPGAs), and digital signal processors (DSPs) (any of which can be referred to as a hardware processor), encoders, circuitry to read encoders, memory devices (including one or more EPROMS, one or more EEPROMs, dynamic random access memory ("DRAM"), static random access memory ("SRAM"), and/or flash memory), and/or any other suitable hardware elements.

Computer-readable media can be any non-transitory media that can be accessed by the computer and includes both volatile and nonvolatile media, removable and non-removable media. By way of example, and not limitation, computer readable media can comprise computer storage media and communication media. Computer storage media can include volatile and nonvolatile, removable and non-removable media implemented in any method or technology for storage of information such as computer readable instructions, data structures, program modules or other data. Computer storage media includes, but is not limited to, RAM, ROM, EEPROM, flash memory or other memory technology, CD-ROM, digital video disk (DVD) or other optical disk storage, magnetic cassettes, magnetic tape, magnetic disk storage or other magnetic storage devices, or any other medium which can be used to store the desired information and which can be accessed by the computer.

Figure 11:
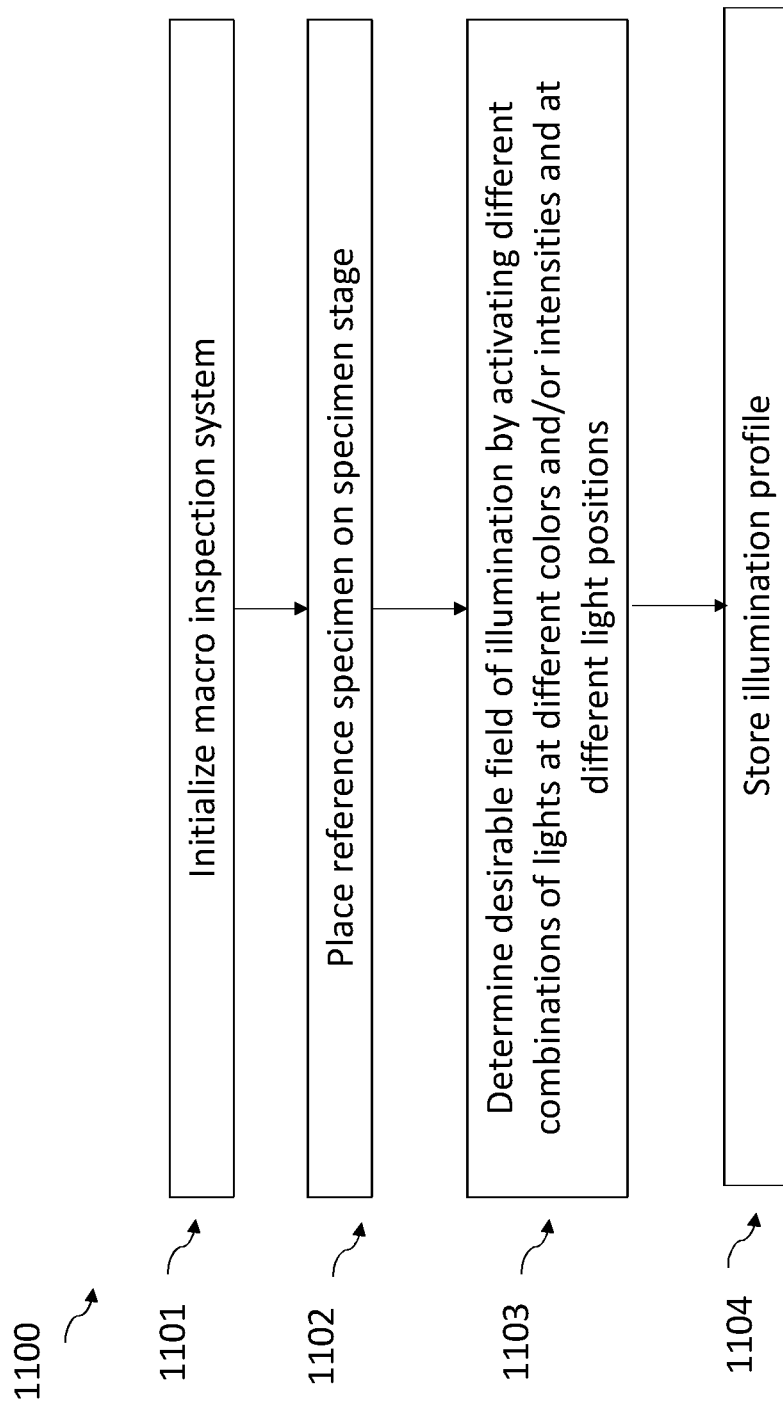
FIG. 11 shows example method steps for calibrating a macro inspection system to achieve different illumination landscapes.

FIG. 11 shows at a high level, an example calibration method 1100 for calibrating macro inspection system to achieve different illumination landscapes, in accordance with some embodiments of the disclosed subject matter. In some embodiments, calibration method 11 can use macro inspection system 10.

At 1101, control module 70 can initialize macro inspection system 10. In some embodiments, initialization can include determining the configuration of lights 16, 50 and/or 60 of macro inspection system 10 (e.g., the total number of lights 16, 50 and/or 60, the address and location of each light 16, 50 and/or 60, the total number and location of light bars 28, the area of projection for each light 16, 50 and/or 60 at each possible position (including height and angle) from the light source to the region where the light is projected (collectively, "configuration information"), and storing the configuration information in local or remote memory.

Figure 12:
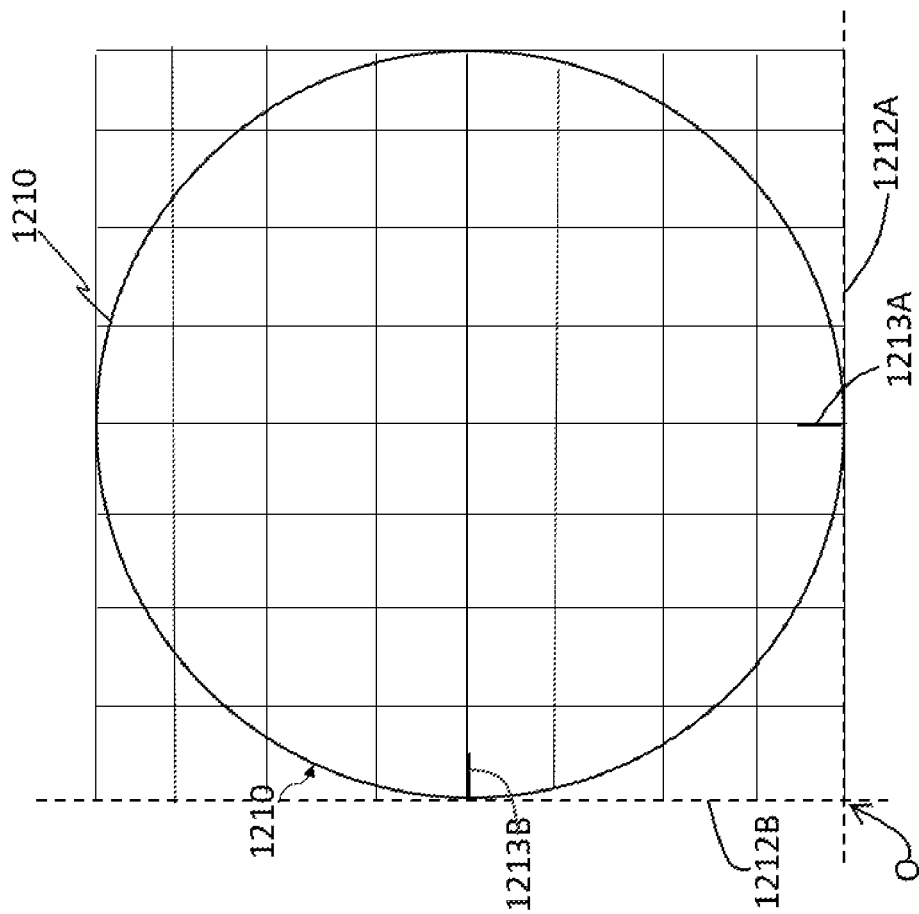
FIG. 12 shows an example coordinate system to define an area of illumination projected by the lights of a macro inspection system.

In some embodiments, as shown for example in FIG. 12, a Cartesian XY coordinate system can be used to define an area of illumination projected by each light 16, 50 and/or 60. The area of illumination is measured in relation to coordinate axes 1212A and 1212B that meet at origin point (O). In some embodiments, the coordinate axes can be a pair of perpendicular lines tangent to a specimen and that extend from reference indices 1213A and 1213B found on a specimen. Note that coordinate axes 1212A and 1212B and origin point O are just examples, an area of illumination can be measured from other coordinate axes and origin point O and/or from another reference point(s). In other embodiments, an area of illuminated can be located by: its polar coordinates in relation to an origin point and/or any other suitable location. In some embodiments, the configuration information at 1101 can be used in relation to the coordinate system defined for macro inspection system 10 to calculate the area of illumination projected by each light 16, 50 and/or 60, and stored for use by macro inspection system 10 to illuminate a specimen S, or a portion thereof.

At 1102, a reference specimen with known features and/or mechanical/physical properties (e.g., size, reflectivity) can be placed on specimen stage 12. Different combinations of lights 16, 50 and/or 60 can be activated at different colors and/or intensities, at different possible distances and angles (collectively, "light position") from the light source to the region where the light is projected to determine a desirable illumination landscape for the reference specimen (at 1103). In some embodiments, the desirable illumination landscape can be determined based on the quality of images captured by image sensor 22, based on the measured intensity of light reflected off a specimen S across each individual pixel or pixel groups of image sensor 22, based on quality of images displayed on a display screen and/or any other suitable metric. In some embodiments, the illumination landscape can be adjusted by manually activating different combinations of lights 16, 50 and/or 60 at different colors and/or intensities and at different possible positions until the desired illumination landscape is achieved. In other embodiments, the illumination landscape can be adjusted by programming a set of conditions (e.g., using control module 70 and configuration information of 1101) to turn on different combinations of lights 16, 50 and or 60 at different colors and/or intensities and at different light positions until a desired illumination landscape is achieved. When the desired illumination landscape for a reference specimen is achieved, the address (or other identifying information) of the activated lights, the intensity level and color of each selected light, as well as position information for each selected light and the distance between stage 12 and lens 14 (collectively "illumination profile"), can be stored (at 1104) by control module 70 for future use.

This process to find and store an appropriate illumination profile can be repeated for different reference specimens representing different classification groups—e.g. by specimen type, by similar mechanical and/or physical specimen properties (e.g., similar reflectivity properties, similar size dimensions), by feature type, by manufacturing process and/or examination stage, by region of interest and/or any other suitable classification group. This process can also be repeated for the same reference specimen to find different illumination profiles that are appropriate for different attributes of the specimen (e.g., as determined by a specimen's mechanical or physical properties); different specimen features that are being examined; different regions of interest on the specimen and/or the manufacturing/examination process that is being examined. In some embodiments, a reference specimen is first put in focus before an illumination profile is calculated. In further embodiments, the distance between specimen stage 12 and lens 14 is adjusted to different preset distances and an illumination profile is calculated for a reference specimen at each preset distance.

In embodiments where a uniform illumination landscape is desired, a reflective specimen that exhibits a uniform reflective background, as determined by standard measurement of reflectivity, can be used to calibrate macro inspection system 10 to provide a uniform illumination landscape. A background can be considered uniform if the reflectivity (e.g., as measured across each individual pixel or pixel groups of image sensor 22) does not vary by more than 5% across the entire field of view of the specimen when viewed on specimen stage 12, and preferably less than 2%. In some embodiments, a reference specimen without a uniform reflective background can be used to calibrate macro inspection system 10 to provide a uniform illumination landscape. When such a specimen is used, lens 14 can be used to create a uniform reflective background by defocusing the specimen to blur any foreign objects and surface irregularities on the specimen to create a more uniform reflective background. The illumination landscape can be adjusted by activating different combinations of lights 16, 50 and/or 60 at different colors and/or intensities and at different possible positions until a uniform illumination landscape is achieved. When a uniform illumination landscape is achieved, the address (or other identifying information) of the activated lights, the intensity and color level of each selected light, as well as light position information for each selected light and the distance between specimen stage 12 and lens 14 can be stored by control module 70 as an illumination profile that provides uniform illumination for macro inspection system 10, a particular specimen, a specimen class, a region of interest, a particular stage in the manufacturing or examining process, and/or for any other suitable classification group.

It should be understood that at least some of the portions of calibration method 1100 described herein can be performed in any order or sequence not limited to the order and sequence shown in and described in connection with FIG. 11, in some embodiments. Also, some portions of process 1100 described herein can be performed substantially simultaneously where appropriate or in parallel in some embodiments. Additionally, or alternatively, some portions of process 1100 can be omitted in some embodiments. Calibration process 1100 can be implemented in any suitable hardware and/or software. For example, in some embodiments, calibration process 1100 can be implemented in macro inspection system 10. Note, that calibration process 1100 is not limited to macroscope inspection systems and can also be implemented in a microscope inspection system.

Figure 13A:
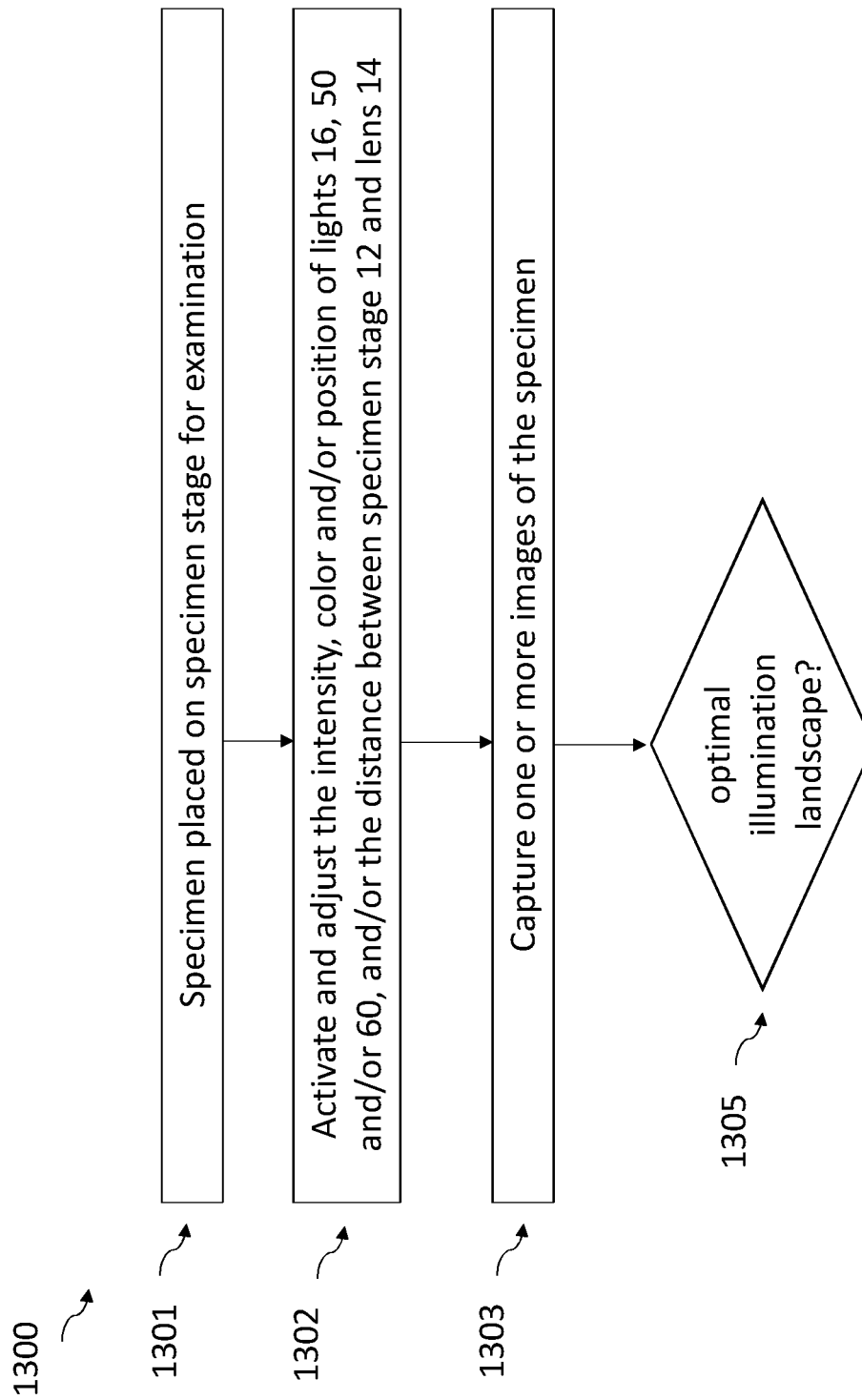
FIG. 13A shows example method steps for illuminating a specimen using a macro inspection system.

FIG. 13A shows at a high level, an example method 1300 for illuminating a specimen using a macro inspection system to achieve a desired illumination landscape ("illumination landscape method 1300"), in accordance with some embodiments of the disclosed subject matter. In some embodiments, illumination landscape method 1300 can use macro inspection system 10.

At 1301, a specimen to be examined can be placed on specimen stage 12. In some embodiments, the specimen is brought into focus before the illumination landscape provided by macro inspection system 10 is adjusted.

At 1302, according to some embodiments, control module 70 can activate and adjust the intensity, color and/or position of lights 16, 50 and/or 60, and/or the distance between specimen stage 12 and lens 14 according to a stored illumination profile that is selected for the specimen. The illumination profile can be selected manually or automatically based on a computer algorithm that assesses different attributes of the specimen (e.g., as determined by one or more physical and/or mechanical properties of a specimen) and/or different goals of the examination and finds a suitable illumination profile. Methods for selecting a suitable illumination profile are further discussed in connection with FIGS. 10, 13B, and 14.

In some embodiments, after selected lights 16, 50 and/or 60 are activated at different colors and/or intensity, and the selected lights, and adjustments are made to the intensity, color and/or light position, and/or the distance between specimen stage 12 and lens 14, according to a selected illumination profile, further adjustments can be to modify the selected illumination profile to achieve a desired illumination landscape. In some embodiments, one or more lights 16, 50 and/or 60 can be activated and adjustments can be made to the intensity, color and/or position of the lights, and/or the distance between specimen stage 12 and lens 14 without reference to any illumination profile. The activations and/or adjustments can be performed manually or automatically.

Once one or more of lights 16, 50 and/or 60 are activated, and adjustments are made to their intensity, color and/or light position, as well as to the distance between specimen stage 12 and lens 14, one or more images of the specimen can be captured and stored for analysis, as at 1303. In some embodiments, the captured specimen images are transmitted to computer analysis system 75.

At 1305, a determination is made by computer analysis system 75 as to whether the applied activation of one or more of lights 16, 50 and/or 60, and adjustments to their intensity, color and/or light position, etc. are sufficient to produce a desired illumination landscape. Such determinations may be made based on an analysis of pixel intensity values for image data received during the image capture step of 1303. If the illumination landscape profile is determined to be sub-optimal, then process 1300 can revert back to step 1302, and further adjustments to the illumination landscape can be made. Steps 1302-1305 can iterate until an optimal illumination profile is achieved. By way of example, if an illumination landscape with a uniform light intensity profile is desired for a particular specimen type, but the image data associated with the captured one or more specimen images indicate that some regions are insufficiently illuminated, then step 1305 can revert back to step 1302. In step 1302, additional changes to light activation, intensity, position (elevation and/or pivot/rotation), etc. can be made. Once changes have been applied to the illumination landscape, step 1303 is repeated and image data is collected from the specimen under the new conditions, e.g., by an image capture device. Again, at step 1305, the new illumination landscape is analyzed to determine if optimal lighting conditions have been achieved.

Different illumination profiles can be selected for a specimen, and for each selected illumination profile, control module 70 can activate and adjust the intensity, color and/or position of lights 16, 50 and/or 60, and/or distance between specimen stage 12 and lens 14 according to the selected profile, and capture and store one or more images of the specimen. As such, the iterative process of steps 1302-1305 can differ with specimen type, as the initially applied illumination landscape that is applied at step 1302 may vary with specimen type, region of interest, a particular stage in the manufacturing or examining process, and/or for any other suitable classification group. In some embodiments, once the illumination is configured according to a selected illumination profile, specimen stage 12 and/or lens 14 can be adjusted to different positions in relation to each other and one or more images of the specimen can be captured at each distance.

Figure 13B:
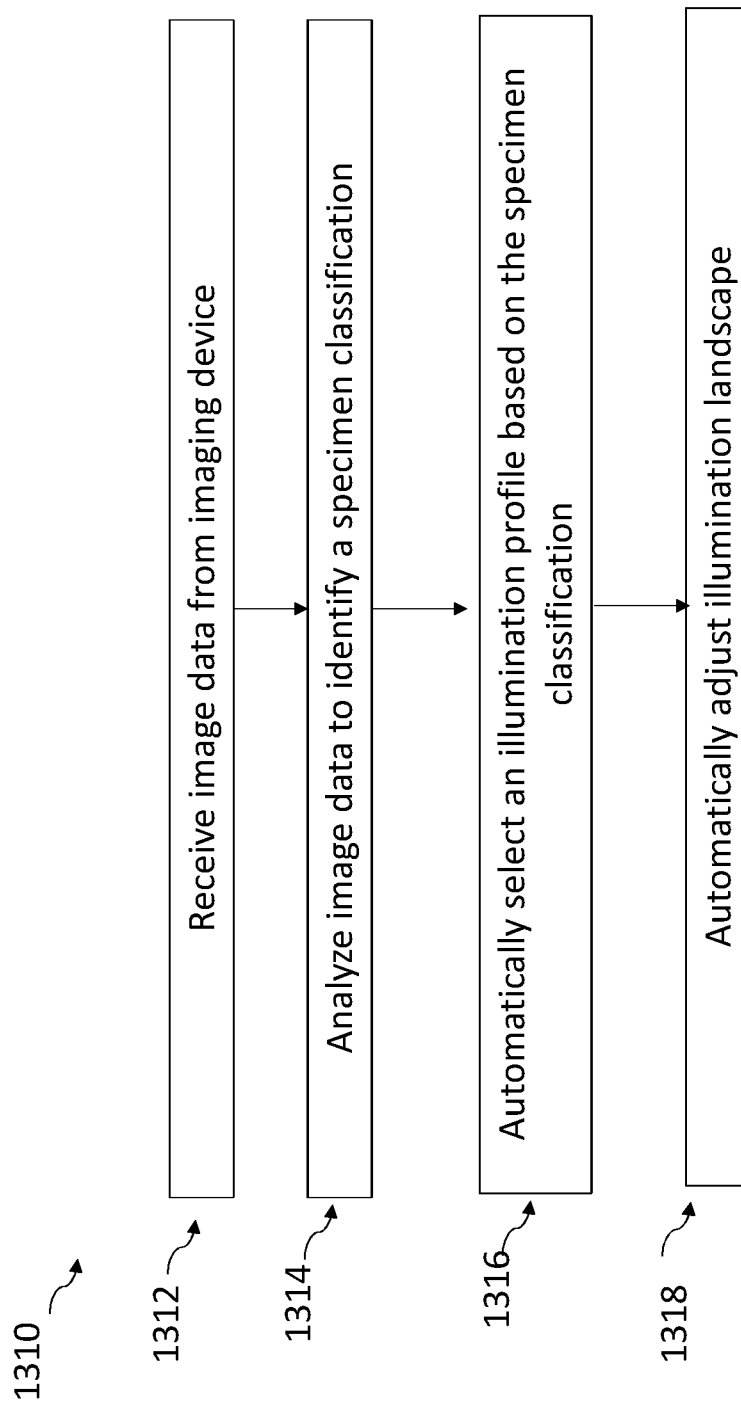
FIG. 13B illustrates steps of an example process for identifying a specimen classification and automatically adjusting an illumination landscape of the macro inspection apparatus.

FIG. 13B illustrates steps of an example process 1310 for identifying a specimen classification and automatically adjusting an illumination landscape of the macro inspection apparatus, according to some aspects of the disclosed technology. Process 1310 begins with step 1312 which image data is received, for example, by an image processing system e.g., image processing module 1034, discussed above. In some approaches, the image data can be included in a received image of a specimen that is taken by an imaging device, as part of macro inspection system 10. The image data can include all or a portion of a specimen that is disposed on a stage of macro inspection system 10. In some instances, that image data may only comprise pixel intensity values, indicating an intensity of light reflected from different portions of a specimen surface.

In step 1314, the image data is analyzed to identify a classification of the specimen. In some instances image analysis may be performed to identify a subset of the specimen, such as a particular region or feature. As discussed below, machine learning classifiers, computer visions and/or artificial intelligence can be used to identify/classify the specimen.

Subsequently, an illumination profile can be automatically selected based on the specimen (or feature) classification and/or a particular stage in the manufacturing or examining process. The specimen/feature classification can be used to query an illumination profile database that contains one or more illumination profiles associated with specimen and/or specimen feature types. By referencing the specimen classification determined in step 1314, a matching illumination profile can be automatically identified and retrieved. As discussed above, the illumination profile can contain a variety of settings data that describe configurations of macro inspection system 10 that can be used to achieve the optimal illumination landscape for the specimen or feature being observed.

It should be understood that at least some of the portions of illumination landscape method 1300 described herein can be performed in any order or sequence not limited to the order and sequence shown in and described in connection with FIGS. 13A and 13B, in some embodiments. Also, some portions of process 1300 described herein can be performed substantially simultaneously where appropriate or in parallel in some embodiments. Additionally, or alternatively, some portions of process 1300 can be omitted in some embodiments. Illumination landscape method 1300 can be implemented in any suitable hardware and/or software. For example, in some embodiments, illumination landscape method 1300 can be implemented in macro inspection system 10. Note, that illumination landscape method 1300 is not limited to macroscope inspection systems and can also be implemented in microscope inspection systems.

Figure 10:
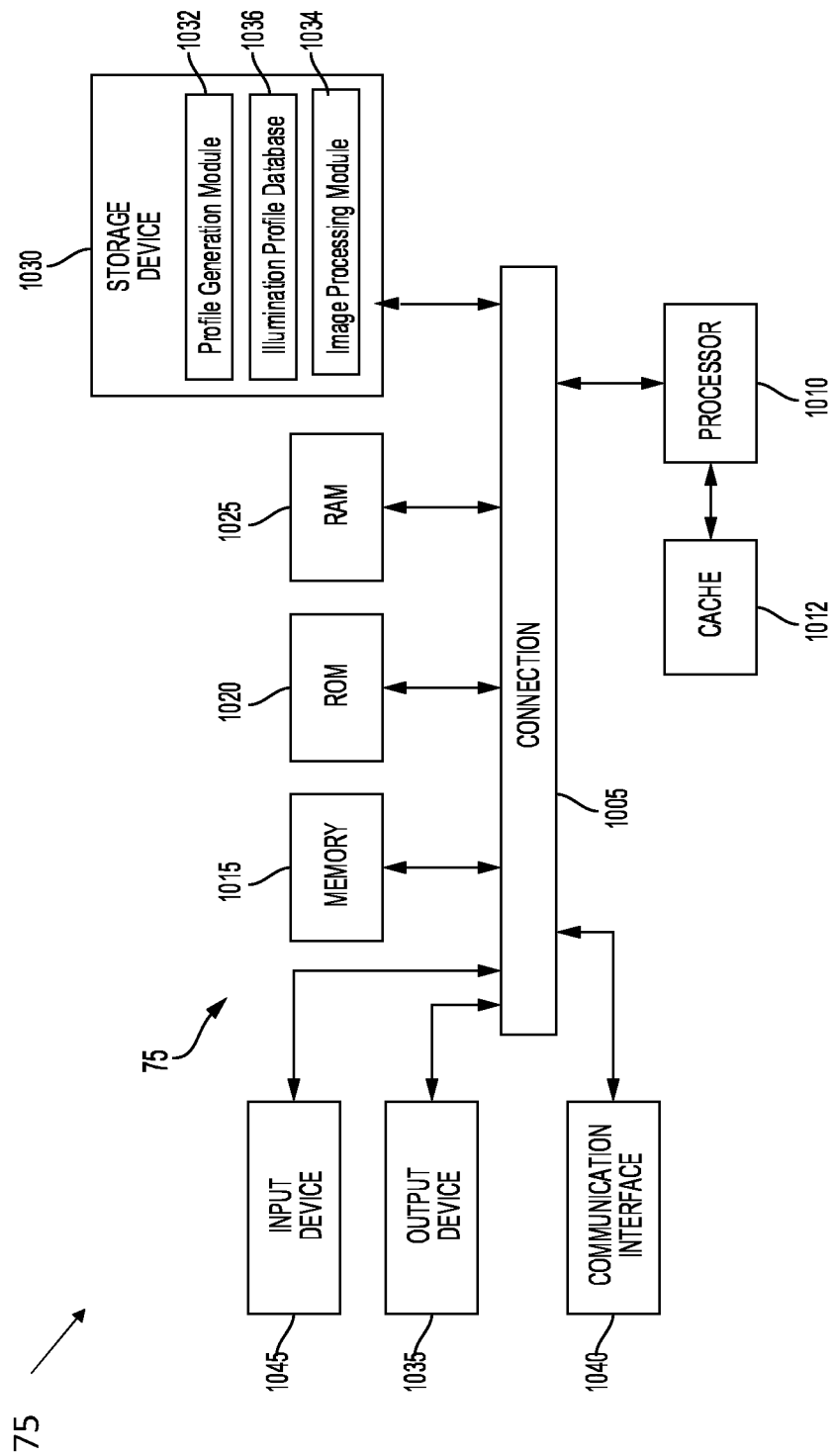
FIG. 10 shows the general configuration of an embodiments of a computer analysis system.

FIG. 10 shows the general configuration of an embodiment of computer analysis system 75, in accordance with some embodiments of the disclosed subject matter. Although computer analysis system 75 is illustrated as a localized computing system in which various components are coupled via a bus 1005, it is understood that various components and functional computational units (modules) can be implemented as separate physical or virtual systems. For example, one or more components and/or modules can be implemented in physically separate and remote devices, such as, using virtual processes (e.g., virtual machines or containers) instantiated in a cloud environment.

Computer analysis system 75 includes a processing unit (e.g., CPU/s and/or processor/s) 1010 and bus 1005 that couples various system components including system memory 1015, such as read only memory (ROM) 1020 and random access memory (RAM) 1025, to processor/s 1010.

Memory 1015 can include various memory types with different performance characteristics. Processor 1010 is coupled to storage device 1030, which is configured to store software and instructions necessary for implementing one or more functional modules and/or database systems, such as profile generation module 1032, illumination profile database 1036, and imaging processing module 1034. Each of these modules can be configured to control processor 1010 as well as a special-purpose processor where software instructions are incorporated into the actual processor design. As such, processor 1010 and one or more of profile generation module 1032, illumination profile database 1036, and imaging processing module 1034 can be completely self-contained systems. For example, imagine processing module 1034 can be implemented as a discrete image processing system, without departing from the scope of the disclosed technology.

To enable user interaction with computer analysis system 75, input device 1045 can represent any number of input mechanisms, such as a microphone for speech, a touch-sensitive screen for gesture or graphical input, keyboard, mouse, motion input and so forth. An output device 1035 can also be one or more of a number of output mechanisms known to those of skill in the art. In some instances, multimodal systems can enable a user to provide multiple types of input to communicate with computer analysis system 75, for example, to convey specimen information relating to a specimen type/classification, or other characteristics. Communications interface 1040 can generally govern and manage the user input and system output. There is no restriction on operating on any particular hardware arrangement and therefore the basic features here may easily be substituted for improved hardware or firmware arrangements as they are developed.

Storage device 1030 is a non-transitory memory and can be a hard disk or other types of computer readable media that can store data accessible by a computer, such as magnetic cassettes, flash memory cards, solid state memory devices, digital versatile disks, cartridges, random access memories (RAMs) 525, read only memory (ROM) 520, and hybrids thereof.

In practice, illumination profile generation module 1032 can be configured to receive a scan of a specimen, or a portion of a specimen (collectively, "specimen image"), from macro inspection system 10, and/or any suitable computer readable media. In some instances, preferred illumination landscapes associated with configurations of the various macro components of macro inspection system 10 can be associated to form an illumination profile, for example, that is associated with the specimen type or classification. Illumination profiles associating illumination landscape settings with specimen classification types can be stored to illumination profile database 1036.

Illumination profiles stored to illumination profile database 1036 can include specific context data such as: a configuration of lights 16, 50 and/or 60 of macro inspection system 10 (e.g., the total number of lights 16, 50 and/or 60, the address and location of each light 16, 50 and/or 60, the total number and location of light bars 28, the area of projection for each light 16, 50 and/or 60 at each possible position that it can be located (including height and angle) from the light source to the region where the light is projected); the range of possible distances between specimen stage 12 and lens 14; regions of interest for particular types of specimen; a particular stage of a manufacturing or examining process that is being examined; a feature that is being examined.

Image processing module 1034 can be used in conjunction with profile generation module 1032 and illumination profile database 1036 to classify a specimen based on the image data received in the specimen image(s) and/or other received specimen characteristics, such as those manually provided by a user, for example, via input device 1045. Additionally, image processing module can be configured to classify specific specimen features, determine other physical and/or mechanical specimen properties (e.g., specimen reflectivity, specimen dimensions). Classifications of specimen types, and specimen features/properties can be stored as part of an illumination profile. As such, various illumination profiles stored in illumination profile database 1036 can contain settings and parameters used to generate an optimal illumination landscape that can be referenced and matched to a sample based on sample type and or specific features or characteristics.

In some aspects, classification of a specimen type and/or features of a specimen can be performed using image processing algorithms that can include computer vision, one or more artificial intelligence algorithm(s) and/or computer algorithms. Classification of a specimen, or features of a specimen, can also be based on, e.g., a computer aided design (CAD) file of a specimen and/or features of a specimen, a specimen layout map identifying features on a specimen, images of known specimens and/or features, and/or information about known specimens (e.g., a specimen's dimensions, the mechanical and/or physical properties of a specimen).

In some instances, machine learning models can be used to perform classification of specimens, specimen features, and/or other specimen characteristics. In some aspects, image data from specimen images can be provided as an input to a machine learning classification system, for example, by image processing module 1034. Classifier output can specify a sample or feature classification that can then be used to reference an illumination profile stored in illumination profile database 1036. By matching the correct illumination profile with the correct sample classification or feature type, the correct illumination landscape can be achieved through the automatic calibration of light intensity, light color, lighting angle, and elevation above the specimen, etc.

As understood by those of skill in the art, machine learning based classification techniques can vary depending on the desired implementation, without departing from the disclosed technology. For example, machine learning classification schemes can utilize one or more of the following, alone or in combination: hidden Markov models; recurrent neural networks; convolutional neural networks; Bayesian symbolic methods; general adversarial networks; support vector machines; image registration methods; applicable rule-based system. Where regression algorithms are used, they may include including but are not limited to: a Stochastic Gradient Descent Regressor, and/or a Passive Aggressive Regressor, etc.

Machine learning classification models can also be based on clustering algorithms (e.g., a Mini-batch K-means clustering algorithm), a recommendation algorithm (e.g., a Miniwise Hashing algorithm, or Euclidean LSH algorithm), and/or an anomaly detection algorithm, such as a Local outlier factor. Additionally, machine learning models can employ a dimensionality reduction approach, such as, one or more of: a Mini-batch Dictionary Learning algorithm, an Incremental Principal Component Analysis (PCA) algorithm, a Latent Dirichlet Allocation algorithm, and/or a Mini-batch K-means algorithm, etc.

Such algorithms, networks, machines and systems provide examples of structures used with respect to any "means for determining an illumination profile for a specimen using artificial intelligence."

In some embodiments, machine learning can be deployed in the creation of illumination profiles. For example, profile generation module 1032 can input the context data, along with the specimen image or data determined from the specimen image ("specimen data") into a trained artificial intelligence algorithm to create one or more appropriate illumination profiles to be applied to illuminate a specimen. In other embodiments, image processing module 1034 can use machine learning models or other computer algorithms to select a predefined illumination profile based on the specimen image, specimen data and/or context data, as discussed above.

Once the desired illumination profile has been selected, e.g., from illumination profile database 1036, the illumination profile data can be transmitted to control module 70. Control module 70 can use this information in connection with process 1300 to apply an illumination profile to illuminate a specimen being examined.

Examples of artificial intelligence based image processing algorithm that can be used by illumination profile generation module 1032 is image registration as described by: Barbara Zitova, "Image Registration Methods: A Survey," *Image and Vision Computing*, Oct. 11, 2003, Volume 21, Issue 11, pp. 977-1000, which is hereby incorporated by reference herein in its entirety. The disclosed methods are just examples and are not intended to be limiting.

In some embodiments, the machine learning algorithms used by illumination profile generation module 1032, and image processing module 1034, including, in some embodiments, an image processing algorithm, is first trained with training data so that illumination profile generation module 1032 can create an appropriate illumination profile for a specimen.

Figure 14:
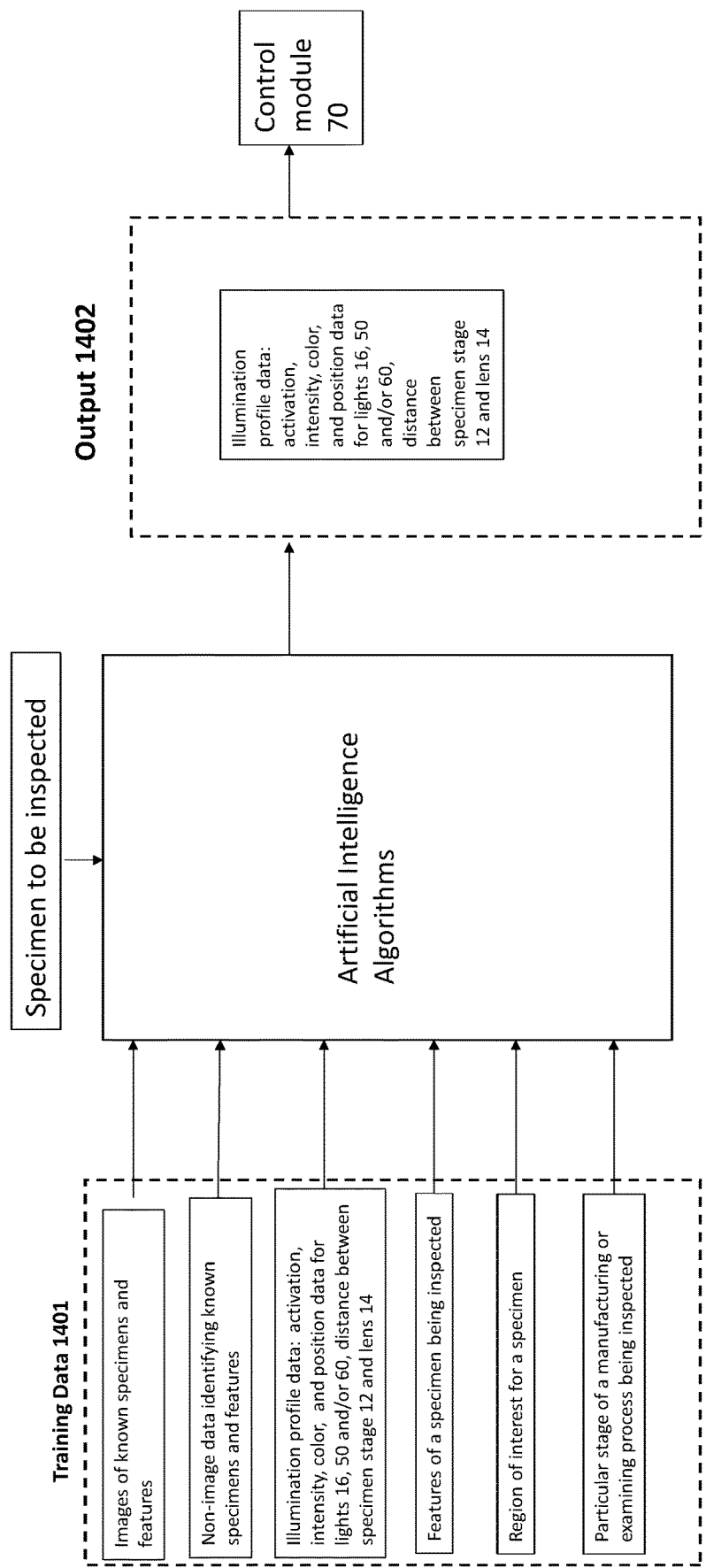
FIG. 14 shows example shows an example training model that uses certain inputs and outputs to feed into an artificial intelligence algorithm to generate one or more illumination profiles.

As shown in FIG. 14, training data 1401 can include labeled images of known specimens and features captured by a macro inspection system according to embodiments of the disclosed subject. The labeled images selected for training can be images of desired quality that show suitable detail based on an inspection objective for the captured images. In some embodiments, training data 1401 can include non-image files identifying the type of specimen and/or features being inspected. Training data can further include for each image: data describing the activation, intensity, color and/or position of lights 16, 50 and/or 60, and/or the distance between specimen stage 12 and lens 14; the features of a specimen being inspected; the region of interest on the specimen being inspected; the particular stage of a manufacturing or examining process being inspected. In some embodiments training data can include physical/mechanical properties of a specimen, and/or any other suitable characteristic used to create an appropriate illumination profile. In some embodiments, training data can also include unlabeled data.

Once the artificial intelligence algorithm used by illumination profile generation module 1032 is trained, it can be applied by illumination profile generation module 1032 to a received specimen scan to create one or more illumination profiles (output data 1402) for each received specimen image. As described above, illumination profile data can include data identifying which lights 16, 50 and/60 to activate, and at what intensity, color and light position. Illumination profile data can also include a distance between specimen stage 12 and lens 14.

Note that automatic macro inspection system 10 can include other suitable components not shown. Additionally or alternatively, some of the components included in automatic mapping macro inspection system 10 can be omitted.

In some embodiments, control module 70 of macro inspection system 10 can be used to locate features of a specimen. Features can refer to known characteristics of a specimen, as well as abnormalities and/or defects. Features can include but are not limited to: circuits, circuit board components, biological cells, tissue, defects (e.g., scratches, dust, fingerprints). Control module 70, using computer vision techniques (e.g., artificial intelligence based algorithms, as discussed above, or other algorithms for image processing or pattern recognition), or other known techniques for image analysis, can detect features on a specimen. For each feature it detects, control module 70 using computer vision or other known image analyses techniques can identify a feature's centroid. As described below, control module 70, can apply different coordinate systems to define the X,Y location of a feature's centroid, as well as the orientation of a feature on a specimen.

Figure 15:
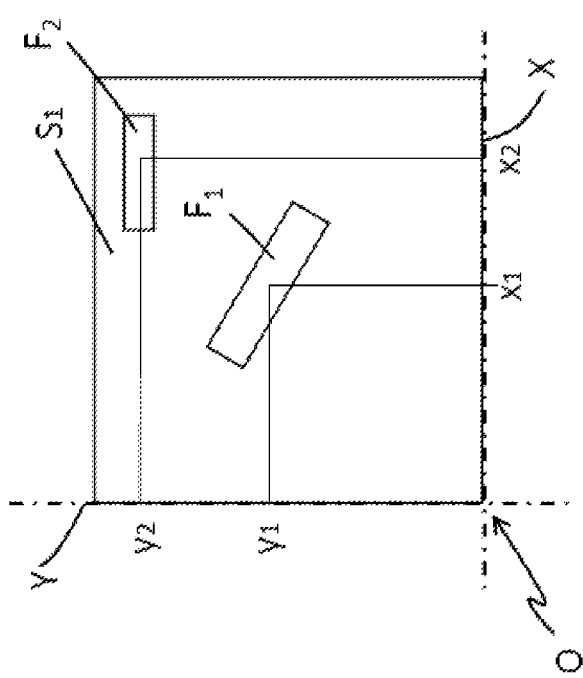
FIG. 15 shows an example coordinate system for a rectangular specimen.

FIG. 15 illustrates a rectangular shaped specimen $S_1$ and an example coordinate system used to locate one or more features (e.g., representative features $F_1$, $F_2$). In some embodiments, control module 70 using computer vision techniques can identify the centroid of each feature $F_1$, $F_2$ on $S_1$. As shown in FIG. 15, a Cartesian XY coordinate system can be used to define the X, Y coordinate location of each centroid F1 (e.g., $x_1$, $y_1$), F2 (e.g., $x_2$, $y_2$). The XY coordinate location of each centroid represents a distance from coordinate axes X, Y that meet at origin point (O). In some embodiments, the coordinate axes can be a pair of perpendicular lines that extend from a corner of specimen S 1. Note that coordinate axes X and Y and origin point O are just examples, the coordinate location of a feature can be measured from other coordinate axes and origin point O and/or from another reference point(s). In other embodiments, a feature can be located by: its polar coordinates in relation to an origin point and/or any other suitable location. Similar methods can be used to find features on differently shaped specimens.

Figure 16B:
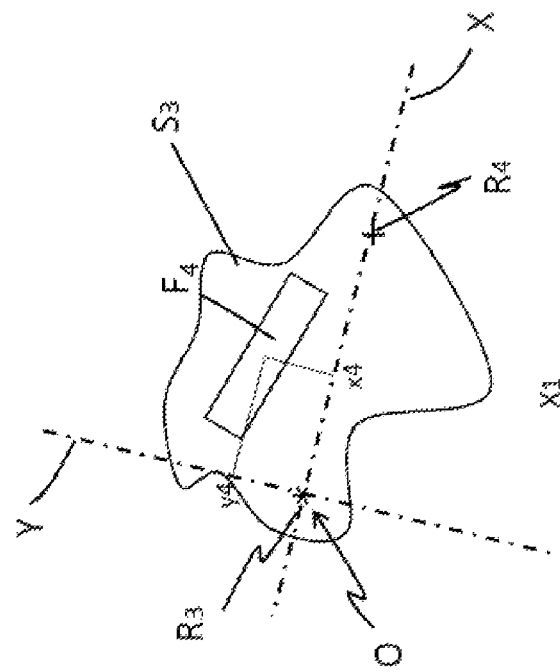
FIG. 16B shows an example coordinate system for an irregularly shaped specimen.
Figure 16A:
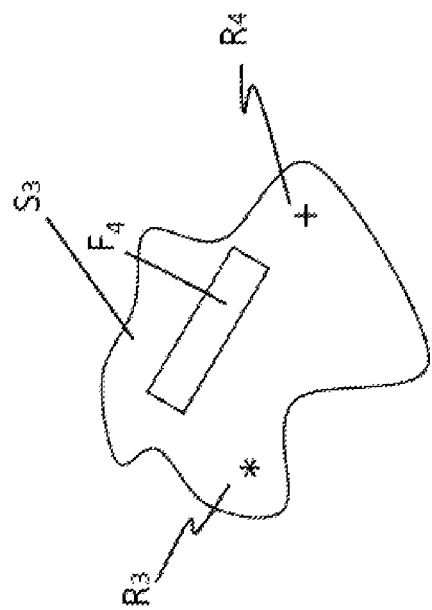
FIG. 16A shows an irregularly shaped specimen.

In some embodiments, as shown for example in FIGS. 16A and 16B, the coordinate axes X, Y used to locate a feature on a specimen can be based on two reference indices (e.g., $R_3$ and $R_4$). For example, a first coordinate axis, as shown in FIG. 16B, can extend through the two reference indices $R_3$ and $R_4$. A second coordinate axis can be positioned perpendicular to the first coordinate axis, so that the intersection of the two axes forms an origin point (O). The second coordinate axis can intersect the first coordinate axis at one of the reference indices R3 and R4, or it can also be positioned anywhere along the first coordinate axis. Specifically, FIG. 16B illustrates an irregularly shaped specimen $S_3$ and example coordinate axes X and Y extending from $R_3$ and R4 used to locate the centroid of one or more features (e.g., representative feature F4). Note, $R_3$ and $R_4$ can be intentionally positioned on a specimen or can be naturally occurring marks on the specimen. In some embodiments, control module 70 can use computer vision algorithms to determine reference marks R3 and R4 that can be used to establish the perpendicular coordinate axes and to locate features on a specimen.

Figure 17:
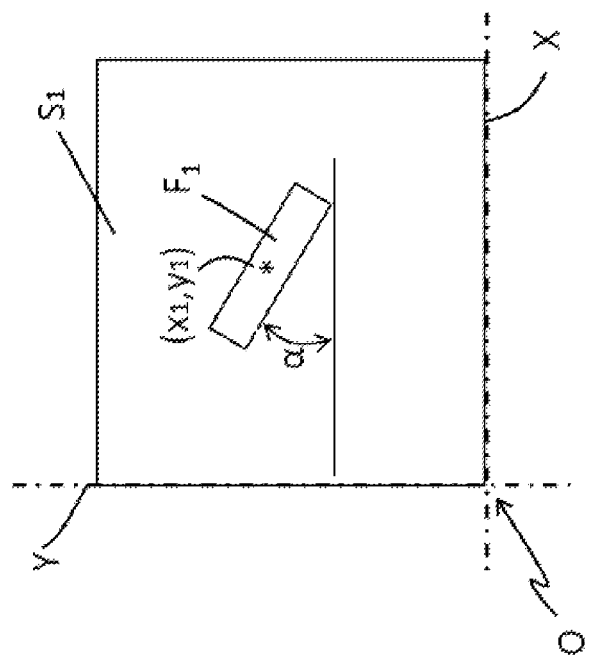
FIG. 17 shows a method for establishing an angle of rotation of a feature on a specimen relative to a coordinate system.

In some embodiments, control module 70 can use computer vision techniques to identify a feature's orientation relative to a pair of coordinate axes. In FIG. 17, the angle of rotation for feature $F_1$ of $S_1$ is shown relative to the coordinate X axis and identified by the angle $\alpha$. This angle $\alpha$ can be calculated by known means of computer vision, and, in such embodiments the $x_1$, $y_1$ coordinates and angle $\alpha$ can uniquely locate the position and orientation of a feature such as feature $F_1$ on a specimen. Although shown with respect to a rectangular specimen $S_1$, it will be appreciated that the calculation of an angle $\alpha$ can be practiced with respect to any shaped specimen.

In some embodiments, a specimen to be inspected can be registered on the specimen stage of macro inspection system 10 in a specific orientation using an indicator on a specimen (e.g., a notch, flat) and aligning the indicator with respect to the known coordinate axes of the specimen stage to locate features on the specimen. In other embodiments, particularly when employing reference marks on the specimen, the specimen can be placed on the specimen stage in any orientation, and the reference marks on the specimen can be employed to establish the coordinate axis, as discussed in connection with FIG. 17.

Note, the methods described herein to locate features of a specimen is not limited to macroscope inspection systems and can also be implemented in microscope inspection systems.

In some embodiments, any suitable computer readable media can be used for storing instructions for performing the functions and/or processes described herein. For example, in some embodiments, computer readable media can be transitory or non-transitory. For example, non-transitory computer readable media can include media such as non-transitory magnetic media (such as hard disks, floppy disks, etc.), non-transitory optical media (such as compact discs, digital video discs, Blu-ray discs, etc.), non-transitory semiconductor media (such as flash memory, electrically programmable read only memory (EPROM), electrically erasable programmable read only memory (EEPROM), etc.), any suitable media that is not fleeting or devoid of any semblance of permanence during transmission, and/or any suitable tangible media. As another example, transitory computer readable media can include signals on networks, in wires, conductors, optical fibers, circuits, and any suitable media that is fleeting and devoid of any semblance of permanence during transmission, and/or any suitable intangible media.

The various systems, methods, and computer readable mediums described herein can be implemented as part of a cloud network environment. As used in this paper, a cloud-based computing system is a system that provides virtualized computing resources, software and/or information to client devices. The computing resources, software and/or information can be virtualized by maintaining centralized services and resources that the edge devices can access over a communication interface, such as a network. The cloud can provide various cloud computing services via cloud elements, such as software as a service (SaaS) (e.g., collaboration services, email services, enterprise resource planning services, content services, communication services, etc.), infrastructure as a service (IaaS) (e.g., security services, networking services, systems management services, etc.), platform as a service (PaaS) (e.g., web services, streaming services, application development services, etc.), and other types of services such as desktop as a service (DaaS), information technology management as a service (ITaaS), managed software as a service (MSaaS), mobile backend as a service (MBaaS), etc.

The provision of the examples described herein (as well as clauses phrased as "such as," "e.g.," "including," and the like) should not be interpreted as limiting the claimed subject matter to the specific examples; rather, the examples are intended to illustrate only some of many possible aspects. A person of ordinary skill in the art would understand that the term mechanism can encompass hardware, software, firmware, or any suitable combination thereof.

Unless specifically stated otherwise as apparent from the above discussion, it is appreciated that throughout the description, discussions utilizing terms such as "determining," "providing," "identifying," "comparing" or the like, refer to the action and processes of a computer system, or similar electronic computing device, that manipulates and transforms data represented as physical (electronic) quantities within the computer system memories or registers or other such information storage, transmission or display devices. Certain aspects of the present disclosure include process steps and instructions described herein in the form of an algorithm. It should be noted that the process steps and instructions of the present disclosure could be embodied in software, firmware or hardware, and when embodied in software, could be downloaded to reside on and be operated from different platforms used by real time network operating systems.

The present disclosure also relates to an apparatus for performing the operations herein. This apparatus may be specially constructed for the required purposes, or it may comprise a general-purpose computer selectively activated or reconfigured by a computer program stored on a computer readable medium that can be accessed by the computer. Such a computer program may be stored in a computer readable storage medium, such as, but is not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of non-transient computer-readable storage medium suitable for storing electronic instructions. Furthermore, the computers referred to in the specification may include a single processor or may be architectures employing multiple processor designs for increased computing capability.

The algorithms and operations presented herein are not inherently related to any particular computer or other apparatus. Various general-purpose systems may also be used with programs in accordance with the teachings herein, or it may prove convenient to construct more specialized apparatus to perform the required method steps and system-related actions. The required structure for a variety of these systems will be apparent to those of skill in the art, along with equivalent variations. In addition, the present disclosure is not described with reference to any particular programming language. It is appreciated that a variety of programming languages may be used to implement the teachings of the present disclosure as described herein, and any references to specific languages are provided for disclosure of enablement and best mode of the present disclosure.

The macro inspection mechanism, method and system have been described in detail with specific reference to these illustrated embodiments. It will be apparent, however, that various modifications and changes can be made within the spirit and scope of the disclosure as described in the foregoing specification, and such modifications and changes are to be considered equivalents and part of this disclosure. The scope of the present disclosure is limited only by the claims that follow.

What is claimed is:

1. An inspection apparatus comprising:
   a stage configured to retain a specimen for inspection;
   an imaging device having a field of view encompassing at least a portion of the stage;
   a lens having a field of view encompassing at least a portion of the stage;
   a plurality of lights disposed on a moveable platform;
   a control module coupled to each of the imaging device, the stage, the moveable platform, and the lens, wherein the control module is configured to control a position of the stage, an elevation of the moveable platform, and a focus of the lens; and
   an image processing system coupled to the control module, wherein the image processing system comprises one or more processors and a non-transitory media comprising instructions that are configured to cause the processors to perform operations for:
   receiving image data from the imaging device, wherein the image data corresponds with at least a partial view of the specimen retained on the stage;
   analyzing the image data to determine a specimen classification corresponding with the specimen retained on the stage; and
   automatically selecting an illumination profile based on the specimen classification by:
   referencing a profile database using the specimen classification; and
   receiving the illumination profile, wherein the illumination profile is associated with the specimen classification in the profile database.

2. The inspection apparatus of claim 1, wherein the instructions are further configured to cause the processors to perform operations for:
   automatically adjusting the position of the stage, using the control module, based on the selected illumination profile.

3. The inspection apparatus of claim 1, wherein the instructions are further configured to cause the processors to perform operations for:
   automatically adjusting the elevation of the moveable platform, using the control module, based on the selected illumination profile.

4. The inspection apparatus of claim 1, wherein the instructions are further configured to cause the processors to perform operations for:
   automatically adjusting the focus of the lens, using the control module, based on the selected illumination profile.

5. The inspection apparatus of claim 1, wherein the instructions are further configured to cause the processors to perform operations for:
   automatically adjusting a pivot of at least one of the plurality of lights disposed on the moveable platform based on the selected illumination profile.

6. The inspection apparatus of claim 1, wherein the imaging device is configured to view the at least a portion of the stage via the lens.

* * * * *